United States Patent [19]
Bryant et al.

[11] Patent Number: 6,060,590
[45] Date of Patent: May 9, 2000

[54] CHITINASE RELATED PROTEINS AND METHODS OF USE

[75] Inventors: Peter J. Bryant, Newport Beach, Calif.; Kazuo Kawamura, Kochi, Japan

[73] Assignee: The Regents of the University of California, Oakland, Calif.

[21] Appl. No.: 09/052,778

[22] Filed: Mar. 31, 1998

[51] Int. Cl.$^7$ ...................... C07K 14/435; C07K 14/475
[52] U.S. Cl. .............................................. 530/399; 530/350
[58] Field of Search ...................................... 530/350, 399

[56] References Cited

PUBLICATIONS

Chan, C.S. et al., Clonal Rearrangement of the T–Cell Receptor Beta–Chain Gene in Hyperplastic Lymphadenopathy Associated with Lung Cancer, *Cancer* 68:1071–1076, 1991.

Hakala, B.E., et al., Human Cartilage gp–39, a Major Secretory Product of Articular Chondrocytes and Synovial Cells, is a Mammalian Member of a Chitinase Protein Family, *J. Bio.Chem.* 268: 25803–25810, 1993.

Kirkpatrick, R.B., et al., Induction and Expression of Human Cartilage Glycoprotein 39 in Rheumatoid Inflammatory and Perifpheral Blood Monocyte–Derived Macrophages, *Exp. Cell Res.* 237:46–54, 1997

Verheijden, G.F., et al., Human Cartilage Glycoprotein–39 as a Candidate Autoantigen in Rheumatoid Arthritis, *Arthritis Rheum.* 40:1115–1125, 1997.

*Primary Examiner*—Robert A. Schwartzman
*Attorney, Agent, or Firm*—Gray Cary Ware & Freidenrich LLP; Lisa A. Haile

[57] ABSTRACT

A family of chitinase related proteins (CHRPs) that promote cell growth and may be useful in wound healing and other indications is provided. In a particular embodiment, imaginal disc growth factor 4 (IDGF4) protein and polynucleotides encoding the protein are provided. The IDGF polypeptides of the family promote cell growth when added exogenously to imaginal disc cell lines. Methods of use for members of the CHRP family, including IDGF1, IDGF2, IDGF3, IDGF4, DS47, gp38k, gp-39, Brp-39, YKL39, YKL40, POSP and homologs or orthologs thereof, are included for accelerating wound healing and tissue growth, modulating angiogenesis and ameliorating cell proliferative disorders in human patients.

1 Claim, 10 Drawing Sheets

GGCACGAG

| ATG | AAG | CTC | TAC | GCC | CTG | TTC | TCC | CTT | CTG | GTG | GGA | TCT | TTG | GCC | ATT |
|-----|-----|-----|-----|-----|-----|-----|-----|-----|-----|-----|-----|-----|-----|-----|-----|
| Met | Lys | Leu | Tyr | Ala | Leu | Phe | Ser | Leu | Leu | Val | Gly | Ser | Leu | Ala | Ile |
| 1   |     |     |     | 5   |     |     |     |     | 10  |     |     |     |     | 15  |     |

| GGT | CAG | ATT | TCC | GCC | GGA | TCT | CAT | CAT | CTA | CTT | TGT | TAC | TAT | GAC |
|-----|-----|-----|-----|-----|-----|-----|-----|-----|-----|-----|-----|-----|-----|-----|
| Gly | Gln | Ile | Ser | Ala | Gly | Ser | His | His | Leu | Leu | Cys | Tyr | Tyr | Asp |
|     |     |     | 20  |     |     |     |     | 25  |     |     |     |     | 30  |     |

| GGC | AAC | AGT | TTT | GTC | CGC | GAG | GGC | CTC | TCC | AAG | CTG | ATC | CTA | ACC | GAT |
|-----|-----|-----|-----|-----|-----|-----|-----|-----|-----|-----|-----|-----|-----|-----|-----|
| Gly | Asn | Ser | Phe | Val | Arg | Glu | Gly | Leu | Ser | Lys | Leu | Ile | Leu | Thr | Asp |
|     |     | 35  |     |     |     |     | 40  |     |     |     |     | 45  |     |     |     |

| CTG | GAG | CCC | GCC | CTG | CAG | TAC | TGC | ACC | CAT | CTG | GTC | TAC | GGA | TAT | GCC |
|-----|-----|-----|-----|-----|-----|-----|-----|-----|-----|-----|-----|-----|-----|-----|-----|
| Leu | Glu | Pro | Ala | Leu | Gln | Tyr | Cys | Thr | His | Leu | Val | Tyr | Gly | Tyr | Ala |
|     | 50  |     |     |     |     | 55  |     |     |     |     | 60  |     |     |     |     |

| GGC | ATT | AAT | CCC | TCG | AGC | AAC | AAG | CTG | GTC | AGC | AAC | AAT | GAG | AAA | CCG |
|-----|-----|-----|-----|-----|-----|-----|-----|-----|-----|-----|-----|-----|-----|-----|-----|
| Gly | Ile | Asn | Pro | Ser | Ser | Asn | Lys | Leu | Val | Ser | Asn | Asn | Glu | Lys | Pro |
| 65  |     |     |     |     | 70  |     |     |     |     | 75  |     |     |     |     | 80  |

| GAC | CTG | GAT | CTG | GGC | AGC | AGC | CTG | TTC | CGC | CAG | GTG | ACC | GGA | TTG | AAG |
|-----|-----|-----|-----|-----|-----|-----|-----|-----|-----|-----|-----|-----|-----|-----|-----|
| Asp | Leu | Asp | Leu | Gly | Ser | Ser | Leu | Phe | Arg | Gln | Val | Thr | Gly | Leu | Lys |
|     |     |     |     | 85  |     |     |     |     | 90  |     |     |     |     | 95  |     |

*FIG. 1A*

CGC AAG TAC CCA GCC CTC AAG GTC CTG CTT AGC GTG GGT GGC GAC AAG
Arg Lys Tyr Pro Ala Leu Lys Val Leu Leu Ser Val Gly Gly Asp Lys
        100                 105                 110

GAC ACC GTG GAT CCA GAG AAC AAG TAT CTG ACC CTG CTG GAG AGC
Asp Thr Val Asp Pro Glu Asn Lys Tyr Leu Thr Leu Leu Glu Ser
    115                 120                 125

AGC AAT GCC AGG ATT CCG TTC ATC AAC AGT GCT CAC TCG CTG GTG AAG
Ser Asn Ala Arg Ile Pro Phe Ile Asn Ser Ala His Ser Leu Val Lys
        130                 135                 140

ACC TAC GGT TTC GAT GGC CTC GAT GGC TGG CAG TTC CCC AAG AAT
Thr Tyr Gly Phe Asp Gly Leu Asp Gly Trp Gln Phe Pro Lys Asn
145                 150                 155                 160

AAG CCA AAG AAG GTG CAC GGC AGC ATT GGC AAG TTC TGG AAG GGA TTC
Lys Pro Lys Lys Val His Gly Ser Ile Gly Lys Phe Trp Lys Gly Phe
        165                 170                 175

AAG AAG ATC TTC AGC GGT GAT CAT CTC GTC GAC GAG AAG GCC GAG GAG
Lys Lys Ile Phe Ser Gly Asp His Leu Val Asp Glu Lys Ala Glu Glu
    180                 185                 190

*FIG. 1B*

```
CAC AAG GAG GCC TTC ACC GCC CTG GTT CGC GAA CTG AAG AAC GCC TTC
His Lys Glu Ala Phe Thr Ala Leu Val Arg Glu Leu Lys Asn Ala Phe
            195                     200                     205

CGT CCC GAT GGC TAC ATC CTG GGT CTC AGT GTC CTG CCC AAT GTG AAC
Arg Pro Asp Gly Tyr Ile Leu Gly Leu Ser Val Leu Pro Asn Val Asn
            210                     215                     220

TCT TCG CTG TTC TTC GAT GTG CCC GCT ATT ATC AAT AAC TTG GAC TAC
Ser Ser Leu Phe Phe Asp Val Pro Ala Ile Ile Asn Asn Leu Asp Tyr
            225                     230                     235                     240

GTG AAC CTG CAC ACC TAC GAC TTC CAG ACC CCC GAG CGC AAC AAC GAG
Val Asn Leu His Thr Tyr Asp Phe Gln Thr Pro Glu Arg Asn Asn Glu
            245                     250                     255

GTG GCC GAC TTC CCG GCA CCG ATC TAC GAG CTG AAC GAG CGC AAT CCG
Val Ala Asp Phe Pro Ala Pro Ile Tyr Glu Leu Asn Glu Arg Asn Pro
            260                     265                     270

GAG TTC AAT GTC AAC TAC CAG GTG AAA TAC TGG ACC GGA AAC CGT GCT
Glu Phe Asn Val Asn Tyr Gln Val Lys Tyr Trp Thr Gly Asn Arg Ala
            275                     280                     285
```

FIG. 1C

```
CCG GCC GCT AAG ATT AAC GTG GGC ATT GCC ACC TAT GGA CGT GCC TGG
Pro Ala Ala Lys Ile Asn Val Gly Ile Ala Thr Tyr Gly Arg Ala Trp
    290                 295                 300

AAA TTG ACC AAG GAT TCG GGA CTG ACT GGA CTT CCA CCG GTT GCC GAG
Lys Leu Thr Lys Asp Ser Gly Leu Thr Gly Leu Pro Pro Val Ala Glu
305                 310                 315                 320

GCT GAT GGT GTG GCT CCT GCC GGA ACC CAG ATA CCC GGA CTT
Ala Asp Gly Val Ala Pro Ala Gly Thr Gln Ile Pro Gly Leu
            325                 330                 335

CTT AGC TGG CCA GAG GTG TGC GCC AAG CTC CCA AAT CCC GCC AAT CAG
Leu Ser Trp Pro Glu Val Cys Ala Lys Leu Pro Asn Pro Ala Asn Gln
            340                 345                 350

CAT CTG AAG GGC GAT GGT GCC GAT GGT CCG CTG CGA AAG GTT GGT GAT CCG ACC
His Leu Lys Gly Ala Asp Gly Pro Leu Arg Lys Val Gly Asp Pro Thr
            355                 360                 365

AAG CGC TTT GGA AGC TAT GCC TAC CCG TCC GCC GAC AGC GGT GAA
Lys Arg Phe Gly Ser Tyr Ala Tyr Pro Ser Ala Asp Asp Ser Gly Glu
    370                 375                 380
```

FIG. 1D

```
AAC GGA GTC TGG GTG GGC TAC GAG GAT CCC GAT ACG GCG GCC ATC AAG
Asn Gly Val Trp Val Gly Tyr Glu Asp Pro Asp Thr Ala Ala Ile Lys
385                     390                 395                 400

GCG GAG TAT GTT AAG CGC GAG GGT CTC GGC GGC ATT GCT GTT GTC GAT
Ala Glu Tyr Val Lys Arg Glu Gly Leu Gly Gly Ile Ala Val Val Asp
            405                 410                 415

CTG AGC TTC GAT GAC TTC CGC GGC GGC TGC ACT GGC CAC GAC AAG TTC
Leu Ser Phe Asp Asp Phe Arg Gly Gly Cys Thr Gly His Asp Lys Phe
                420                 425                 430

CCC ATC CTG CGC CAG GTC AAG AGC AAG TTG TAG AGCTCCTCAT CCTCCCTG
Pro Ile Leu Arg Gln Val Lys Ser Lys Leu
                435                 440

ATTCTTTTCC GGAACGGAAG AACAAACGTG TTTTTATTTG CCCCGCTGTT TTTTTTAT
ATGTAATTGA CTCAACGCAAA ACGCGAAATG CAAATTTAAA SSAATATA
ACATTGACAC CAAAAAAAAA AAAAAAAA
```

FIG. 1E

```
IDGF1  ------PNKYVELLENRTAQQNFIDSSMILLKRNGFDGLDLAFQLPRNKPRKVHGSLGSah------   164
IDGF2  ------NKYIDLLEGEKVRQIGFIRSAYDLVKTYGFDGLDLAYQFPKNKPRKVHGDLGLdhp----   167
IDGF3  ------NQYIKLIESGQQGHRRFIESARDIVRRYNFDGLDLAIQLPRNKPRKVHGDVGSg-------  168
IDGF4  ------NNKYLTLLESSNARIPFINSAHSLVKTYGFDGLDLGWQFPKNKKVHGSIGKpe--------  171
DS47   dkdakelPNKYIELLESPTGRTRFVNTVYSLVKTYGFDGLDVAWQFPKNKKVHSGIGN---------  180
C'ase  ------SSKYSHMVAQKSTRMSFIRSVVSFLKKYDFDGLDLDWEYPgaadrgg--------------  155

IDGF1  YWKSFKKLFTGDFVVDPQAEEHKSQFTDLVGNIKNAFRSANL---MLSLTVLPNVNSTWY   221
IDGF2  AWKSIKKLFTGDFIVDPHAALHKEQFTALVRDVKDSLRADGF---LLSLTVLPNVNSTWY   224
IDGF3  AWKSFKKFTGDFIVDTESETHKGQVTALIKDLSAALKQNDL---LLSLTVLPNVNSSWY   225
IDGF4  FWKGFKKIFSGDHIVDEKAEEHKEAFTALVRELKNAFRPDGY---ILGLSVLPNVNSSLF   228
DS47   LWKGFKKVFSGDSIVDEKSEEHKEQFTALLRDVKNAFRPDNL---LLSTTVLPNVNSSLF   237
C'ase  -----------SFSDKFLYLVQELRRAFirvgkgweLTAAVPLANFRLMEG           197

IDGF1  FDVPKLHPQFDYINLAAFDFLTPLRNPEEADFTAPIFFQD-EQNRLPHLNVEFQINYWLQ   280
IDGF2  FDIPALNGLVDFVNLATFDFLTPARNPEEADYSAPIYHPDgSKDRLAHLNADFQVEYWLS   284
IDGF3  YDAPSIAPSLDFINLGTFDFLTPQRNPEEADFSAPTYEAV-GQNRLGHYNLNFQMEHWLL   284
IDGF4  FDVPAIINNLDYVNLHTYDFQTPERNNEVADFPAPIYE----LNERNPEFNVNYQVKYWTG   285
DS47   YDIPAVVNYLDFVNLGTFDFFTPQRNPEIADYAAPIYE----LSERNPEFNVAAQVKYWLR   294
C'ase  YHVPELCQELDALHVMSYDLRgnwagfadvhsplykrph---DQWAYEKLNVNDGLHLWEE   255
```

FIG. 4C

```
IDGF1  NHCPGQKLNLGIASYGRAWKLSKGSGLSGAPIVHETCGVAPGG------GLLSWPEICS        333
IDGF2  QGFPSNKINLGVATYGNAWKLTKDSGLEGVVPETSGPAPEGFQ-SQKPGLLSYAEICG        343
IDGF3  QRVPANKINIGIATYGRSWKMSKDSGDSGMPVVPSTQGPAPAGPQ-SKQEGLINWAEICS        343
IDGF4  NRAPAAKINVGIATYGRAWKITKDSGLTGLPPVAEADGVAPAGTQ-TQIPGLLSWPEVCA       344
DS47   NNCPASKINVGVATYGRPWKLITDDSGDTGVPPVKDVKDEAPVGGN-TQVPGIYSWPEVCA       353
C'ase  KGCPSNKLVVGIPFYGRSFTLSAGNNNYGlgtfinkeaggdpapyTNATGFWAYYEICT         315

IDGF1  KLSQNASAQYRGELAPLRKVTDLTQKYGNYALRPADDNGDFGVWLSFDDPFAGIKAVYA        393
IDGF2  KLSNPONQFLKGNESPLRKVSDPTKRFGIAYRPVDGQITEGIWVSYDDPDSASNKAAYA        403
IDGF3  LMPNPSNSNARGPNAPVKRVVDPTKRYGSYAFRAADENGHGLWISYDPPDSASSKAMYA        403
IDGF4  KLPNPANQHLKGADGPLRKVGDPTKRFGSYAYPSADDSGENGVWVGYEDPDTAAIKAEYV      404
DS47   LLPNQNNAYLKGANAPLIKVQDPAKRFGSYAYRAADKKGDNGIWVSFEDPDIAADKAGYV       413
C'ase  EVDKDDSGWTKkwdeqgkcpyaykgtq------WVGYEDPRSVEIKMNWI                  359

IDGF1  KGKGLGGGIALFDLSYDDFRGLC--TGQKYPILRSIKY------                        428
IDGF2  RVKNLGGVALFDLSYDDFRGQC--SGDKYPILRAIKYRL-----                        440
IDGF3  RARNLGGVALFDLSYDDFRGQC--TNDRFPMLRAIKYRLl----                        441
IDGF4  KREGLGGIAVVDLSFDDFRGGCtGHDKFPILRQVKSKL-----                         442
DS47   RTENLGGVALFDLSYDDFRGLC--TNEKYPILRAIKYRLtn---                        452
C'ase  KQKGYLGAMTWAIDMDDFQGLCgeknplikilhkhmssytv + 154 amino acids         554
```

FIG. 4D

CHITINASE RELATED PROTEINS AND METHODS OF USE

This invention was made with Government support under Grant (or Contract) No. HD27173, awarded by the National Institutes of Health. The Government has certain rights in this invention.

TECHNICAL FIELD

This invention relates generally to growth factors and specifically to chitinase related proteins (CHRPs) which include imaginal disc growth factors (IDGFs) isolated from Drosophila and related family members in other species (e.g., manmals) and methods of use thereof.

BACKGROUND

Growth factors can be broadly defined as multifunctional, intercellular signaling polypeptides that control both the ontogeny and maintenance of tissue form and function. Growth factors may act locally or at a distance, and they share a number of common biological properties. They often exert their biological actions at very low concentrations because their action is mediated by their association with specific, high-affinity receptors expressed by the target cell type. The function of the growth factor receptor is not only to interact specifically with the ligand on the outside of the cell but also to generate an intracellular signal on the inside of the cell. This generation of growth factor receptor-mediated intracellular signals, and their interpretation by the responding cell, leads to the modification of target cell behavior. Some growth factors are highly restricted in the range of cells on which they act, whereas others can regulate the behavior of many different cell types. Some growth factors are found to be widespread in their expression and distribution in the developing embryo and fully developed adult. The biological actions of growth factors are not confined to the regulation of cell replication, but can extend to a wide variety of cell functions including differentiation, migration and gene expression.

Growth factors have generally been first identified by their ability to stimulate proliferation in cell cultures that have become quiescent as a result of contact inhibition. Most have been isolated from mammalian sources and have been identified by their effects on mammalian cells. Some growth factor-like molecules have been identified in Drosophila by homology searching and by genetic analysis. Examples include the EGF-related products of the spitz (Schweitzer, et al., *Genes Dev.*, 9:1518, 1995) and gurken (Neuman-Silverberg, et al., *Cell*, 75:165, 1993) genes; and the TGF-β family member produced by the dpp gene (Cohen, *Development*, 107:65, 1989). However, none of these has been clearly shown to have mitogenic activity as expected of a growth factor.

Drosophila larvae have ten pairs of imaginal discs which give rise to the eyes/antennae, the legs, the halteres, the wings, various head structures and a single genital disc. Imaginal discs develop from patches of cells that proliferate extensively during larval development. Cell proliferation in imaginal discs is regulated locally by cell interactions as part of the mechanism that leads to the development of spatial patterns of differentiation within the Drosophila epithelium (Hakala, et al., *J. Biol. Chem.* 268:25803, 1993). These interactions are known to involve signaling pathways mediated by secreted factors which include the products of the hh (Capdevila, et al., *EMBO J.*, 13:4459, 1994), dpp (Pignoni, et al., *Development*, 124:271, 1997) and wg (Neumann, et al., *Development*, 122:1781, 1996) genes. Such factors lead to excess cell proliferation when ectopically expressed, but these effects are localized and may be an indirect result of effects on patterning rather than an indication of conventional growth-factor activity. Growth factors as defined in the mammalian cell paradigm have not been previously identified from invertebrates.

SUMMARY OF THE INVENTION

The present invention is based on the identification of a family of chitinase-related proteins (CHRPs). Some of the original family members were isolated from Drosophila imaginal disc cell cultures and have been called imaginal disc growth factors (IDGFs). These factors cooperate with insulin to stimulate the proliferation, polarization and motility of imaginal disc cells and are the first polypeptide growth factors isolated from invertebrates. The IDGF family in Drosophila includes at least five members that are expressed in the embryonic amnioserosa and in the fat body of the embryo and larva. The invention describes an IDGF4 polypeptide from Drosophila and the gene encoding the polypeptide. The invention further describes methods of use for IDGF1, IDGF2, IDGF3 and DS47 (a 47-kDa glycoprotein from Drosophila Schneider line-2 cells) polypeptides from Drosophila and gp38k, gp-39, Brp-39, YKL39, YKL40, POSP and homologs or orthologs thereof. The polypeptides are useful for developing antibodies that bind to the polypeptides, as well as providing diagnostic and therapeutic methods for cell proliferation-associated pathologies. The original isolation of IDGFs in Drosophila allows the identification and isolation of other CHRP family members in other species, including mammals, and specifically, humans.

The present invention includes methods of use for these proteins and the genes encoding them, based on the prediction that the mammalian CHRPs will have mitogenic activity as observed with the Drosophila IDGFs.

In a first embodiment, the invention provides a substantially purified IDGF4 polypeptide and nucleic acid encoding the IDGF4 polypeptide. In accordance with another aspect of the invention, an expression vector containing IDGF4 nucleic acid is provided. Also included is a method for producing the IDGF4 polypeptide. In another aspect, the invention provides antibodies that bind to CHRP polypeptides.

In another embodiment, the invention provides a method for accelerating tissue growth in an animal or human subject, by contacting the appropriate tissue with a therapeutically effective amount of a composition containing CHRP polypeptide, or a biologically finctional fragment thereof, or by transfecting appropriate cells or tissues with polynucleotides encoding or inducing the production of such polypeptides. Clinical applications of such treatment could be to promote wound healing, bone or cartilage repair, angiogenesis, or tissue growth in reconstructive or plastic surgery. Animal applications could be to stimulate muscle growth for increased meat production, gonad tissue for increased egg or sperm production, or mammary tissue for increased milk production.

In another embodiment, the invention provides a method for inhibiting abnormal growth, including cancer and metastasis, in a subject in need of such treatment, by treatment with a composition containing an agent that regulates CHRP production or activity.

In yet another embodiment, the invention provides a method for identifying a compound that modulates CHRP expression or activity by incubating components comprising the compound and CHRP polypeptide, or cell expressing CHRP, under conditions sufficient to allow the components to interact and determining of the effect of the compound on the CHRP gene or polypeptide, respectively.

The invention further provides a method of detecting a CHRP-specific cell component in a sample by contacting a sample suspected of containing CHRP with a reagent that binds to the CHRP-specific component and detecting binding of the reagent to the component.

The invention further provides a method of promoting insect cell or tissue growth in vitro by contacting the cell or tissue with a growth-promoting amount of a compound containing CHRP polypeptide. In another aspect, the invention provides a method of promoting mammalian cell or tissue growth by contacting the cell or tissue with a growth-promoting amount of a compound containing CHRP polypeptide.

In another embodiment, the invention provides a method of diagnosing a pathological state in a subject suspected of having pathology characterized by a cell proliferative disorder associated with CHRP, which includes obtaining a sample suspected of containing CHRP from the subject, determining the level of CHRP in the sample and comparing the level of CHRP in the sample to the level of CHRP in a normal standard sample.

In another embodiment, the invention provides a kit useful for the detection of CHRP polypeptide, nucleic acid encoding CHRP and antibodies that bind to CHRP.

In yet another embodiment, the invention provides a kit useful for the detection of CHRP nucleic acid which includes one or more containers containing a polynucleotide that hybridizes to CHRP nucleic acid.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A–1E show a nucleic acid sequence for the IDGF4 gene (SEQ ID NO:1) and the deduced amino acid sequence of the IDGF4 polypeptide (SEQ ID NO:2).

FIG. 4A shows a genomic map of cytological region 36A2-4 containing IDGF1–3 from chromosome 2. Top row shows subclones of the P1 clone DS02780 (identified from Flybase). The position of sequence tagged sites (STSs) within the P1 clone, compared with the STS framework map, shows that the second-chromosome centromere is to the right of this set of clones. Bottom row shows IDGF1, 2 and 3 transcripts predicted from open reading frames and confirmed by cDNA sequencing. All transcripts are transcribed in the same direction, and the right-most intron is in a conserved position relative to the coding sequence.

FIGS. 4B–4D show MACAW alignment (Schuler, et al., *Proteins Struct. Funct. Genet.*, 9:180, 1991) of the predicted sequences of the microsequence from the purified fraction ("Micro"), four IDGFs, Drosophila DS47 (Kirkpatrick, et al., *Gene*, 153:147, 1995) and authentic gut chitinase (Case) from *Manduca sexta* (Kramer, et al., *Insect Biochem. Mol. Biol.*, 23:691 1993)(SEQ ID NOS:2,11–14. Darkness of shading reflects match with IDGF1. Asterisks indicate the positions of residues that have been shown to be required for catalytic activity in bacterial chitinase (Watanabe, et al., *J. Biol. Chem.*, 268:18567, 1993). The first three match the required residues in chitinases, however the fourth is E (glutamic acid) in chitinases and Q (glutamine) in IDGFs. All four predicted IDGF sequences and DS47 contain an N-terminal signal sequence, and a single consensus motif (arrowhead) for N-linked glycosylation (Kirkpatrick, et al., *Gene*, 153:147, 1995) that is not present in chitinase.

DETAILED DESCRIPTION OF THE INVENTION

Figure 2A:
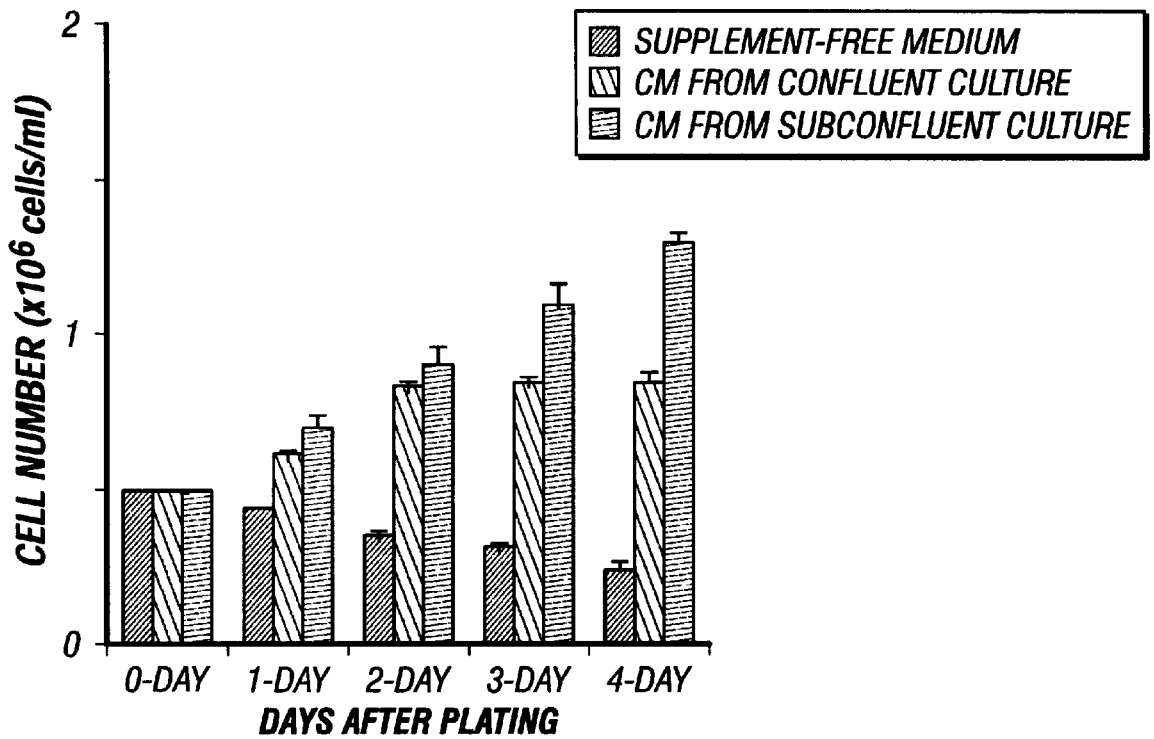
FIG. 2A shows a bar graph indicating the effect of conditioned medium (CM) on proliferation of the imaginal disc cell line C1.8+. C1.8+ cells were plated at $0.5 \times 10^6$ cells/ml in 24-well plates and allowed to proliferate for four days in supplement free medium (SFM), CM prepared from confluent cultures, and CM prepared from subconfluent cultures. The bars represent the standard deviation.

The present invention originated from the discovery and cloning of a family of Drosophila chitinase related protein (CHRP) genes which encode the first polypeptide growth factors identified from invertebrates. These genes, referred to as IDGF1–4 and DS47, encode polypeptides which promote cell growth, motility and morphogenesis. These IDGF polypeptides are expressed at all stages of Drosophila development and particularly in mid-larval stages. Recombinantly produced IDGFs promote cell growth when added exogenously to imaginal disc cell lines. A synergistic growth promoting effect was observed when IDGFs were added in combination with insulin. The demonstration of mitogenic activity of the Drosophila CHRP family members raises the possibility that mammalian family members have similar functions, and that this mitogenic activity may be important in cell proliferation-associated pathologies.

IDGF4 Nucleic Acid, Polypeptides and Method of Expression

In one embodiment, the invention provides an isolated polynucleotide sequence encoding IDGF4 polypeptide. An exemplary IDGF4 polypeptide of the invention has an amino acid sequence as set forth in SEQ ID NO:2. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode IDGF4. It is understood that all polynucleotides encoding all or a portion of IDGF4 are also included herein, as long as they encode a polypeptide with IDGF4 activity (e.g., modulate cellular proliferation). Such polynucleotides include naturally occurring, synthetic, and intentionally manipulated polynucleotides. For example, IDGF4 polynucleotide may be subjected to site-directed mutagenesis. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of IDGF4 polypeptide encoded by the nucleotide sequence is functionally unchanged. Also included are nucleotide sequences which encode IDGF4 polypeptide, such as SEQ ID NO:1. In addition, the invention also includes a polynucleotide encoding a polypeptide having the biological activity of an amino acid sequence of SEQ ID NO:2 and having at least one epitope for an antibody immunoreactive with IDGF4 polypeptide. Assays provided herein can be used to detect the presence IDGF4 in a cell proliferation-associated pathology.

The invention includes polypeptides having substantially the same as the amino acid sequence set forth in SEQ ID NO:2 or functional fragments thereof, or amino acid sequences that are substantially identical to SEQ ID NO:2. By "substantially the same" or "substantially identical" is meant a polypeptide or nucleic acid or a region thereof exhibiting at least 50%, preferably 60%, more preferably 75% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides. The invention includes other CHRP family members having functional activity of the CHRPs described herein, e.g., stimulation of cell proliferation, motility and morphogenesis. By "substantially identical" is also meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein assayed, (e.g., as described herein). Preferably, such a sequence is at least 50%, 60%, 75% or more identical at the amino acid level to SEQ ID NO:2.

The IDGFs belong to a family of chitinase-related protens (CHRPs) that includes several mammalian secreted glycoproteins of ill-defined function, none of which have been previously identified as a growth factor. The family includes a heparin-binding glycoprotein (gp38k; 22% identical to IDGF3) produced during differentiation of vascular smooth muscle cells (Shackelton, et al., *J. Biol. Chem.*, 270:13076, 1995); a major secretory product (HCgp-39; 21% identical to IDGF3) of articular chondrocytes and synovial cells from patients with arthritis (Hakala, et al., *J. Biol. Chem.* 268:25803, 1993); and a protein (Brp-39; 19% identical to IDGF3) secreted by certain murine mammary tumors (Morrison, et al., *Oncogene*, 9:3417, 1994). Closely related proteins (YKL39 and YKL40; 17% and 21% identical to IDGF3) accumulate in chondrocyte conditioned medium (Hu, et al., *J. Biol. Chem.*, 271:19415, 1996), and others are secreted by the mammalian oviduct (POSP; Buhi, et al., *Biol. Reprod.*, 55:1305, 1996). Thus, the mammalian counterparts of the CHRP family of the invention likely will have homology in the range of about 15–40% to the Drosophila CHRPs described herein. However, all CHRP family members included in the invention, whether isolated from Drosophila, mammalian or other species, have growth factor activity.

Homology is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications.

By a "substantially pure polypeptide" is meant an IDGF4 polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, IDGF4 polypeptide. A substantially pure IDGF4 polypeptide may be obtained, for example, by extraction from a natural source (e.g., an insect cell); by expression of a recombinant nucleic acid encoding an IDGF4 polypeptide; or by chemically synthesizing the protein. Purity can be measured by any appropriate method, e.g., those described in column chromatography, polyacrylamide gel electrophoresis, or by HPLC analysis.

IDGF4 polypeptides of the present invention include peptides, or full length protein, that contains substitutions, deletions, or insertions into the protein backbone, that would still leave an approximately 50%–70% homology to the original protein over the corresponding portion. A yet greater degree of departure from homology is allowed if like-amino acids, i.e. conservative amino acid substitutions, do not count as a change in the sequence. Examples of conservative substitutions involve amino acids that have the same or similar properties. Illustrative amino acid conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation, for example of possible modifications. The modified peptides can be chemically synthesized, or the isolated gene can be site-directed mutagenized, or a synthetic gene can be synthesized and expressed in bacteria, yeast, baculovirus, tissue culture and so on.

In addition to polypeptides of the invention, specifically disclosed herein is a DNA sequence for IDGF4 represented by SEQ ID NO:1. DNA sequences of the invention can be obtained by several methods. For example, the DNA can be isolated using hybridization or computer-based techniques which are well known in the art. These include, but are not limited to: 1) hybridization of genomic libraries with probes to detect homologous nucleotide sequences; 2) antibody screening of expression libraries to detect cloned DNA fragments with shared structural features; 3) polymerase chain reaction (PCR) on genomic DNA using primers capable of annealing to the DNA sequence of interest; and 4) computer searches of sequence databases for similar sequences.

The polynucleotide encoding IDGF4 includes the nucleotide sequence in FIG. 1 (SEQ ID NO:1), as well as nucleic acid sequences complementary to that sequence. When the sequence is RNA, the deoxyribonucleotides A, G, C, and T of SEQ ID NO:1 are replaced by ribonucleotides A, G, C, and U, respectively. Also included in the invention are fragments (portions) of the above-described nucleic acid sequences that are at least 15 bases in length, which is sufficient to permit the fragment to selectively hybridize to DNA that encodes the protein of FIG. 1 (e.g., SEQ ID NO:2). "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Oligonucleotides encompassed by the present invention are also useful as primers for nucleic acid amplification reactions. In general, the primers used according to the method of the invention embrace oligonucleotides of sufficient length and appropriate sequence which provides specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product that is substantially complementary to a target nucleic acid strand. The oligonucleotide primer typically contains 15–22 or more nucleotides, although it may contain fewer nucleotides as long as the primer is of sufficient specificity to allow essentially only the amplification of the specifically desired target nucleotide sequence (i.e., the primer is substantially complementary).

Amplified products may be detected by Southern blot analysis, without using radioactive probes. In such a process, for example, a small sample of DNA containing a very low level of IDGF4 nucleotide sequence is amplified and analyzed via a Southern blotting technique known to those of skill in the art. The use of non-radioactive probes or labels is facilitated by the high level of the amplified signal.

IDGF4 polynucleotide of the invention is derived from an insect (e.g., Drosophila). Screening procedures which rely on nucleic acid hybridization make it possible to isolate any gene sequence from any organism, provided the appropriate probe is available. For example, it is envisioned that such probes can be used to identify other members of the CHRP family of growth factors in insects or, alternatively, in other organisms such as mammals, e.g., humans. In accomplishing this, oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of DNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned.

DNA sequences encoding IDGF4 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the IDGF4 polynucleotide sequences may be inserted into a recombinant expression vector. The term "recombinant expression vector" refers to a plasmid, virus or other vehicle known in the art that has been manipulated by insertion or incorporation of the IDGF4 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the 17-based expression vector for expression in bacteria (Rosenberg, et al, *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., 17, metallothionein I, or polyhedrin promoters).

Polynucleotide sequences encoding IDGF4 can be expressed in either prokaryotes or eukaryotes. Hosts can include microbial, yeast, insect and mammalian organisms. Such vectors are used to incorporate DNA sequences of the invention.

Methods which are well known to those skilled in the art can be used to construct expression vectors containing the IDGF4 coding sequence and appropriate tanscriptional/translational control signals. These methods include in vitro recombinant DNA techniques, synthetic techniques, and in vivo recombination/genetic techniques. (See, for example, the techniques described in Maniatis et al., 1989, *Molecular Cloning A Laboratory Manual*, Cold Spring Harbor Laboratory, N.Y.)

A variety of host-expression vector systems may be utilized to express the IDGF4 coding sequence. These include but are not limited to microorganisms such as bacteria transformed with recombinant bacteriophage DNA, plasmid DNA or cosmid DNA expression vectors containing the IDGF4 coding sequence; yeast transformed with recombinant yeast expression vectors containing the IDGF4 coding sequence; plant cell systems infected with recombinant virus expression vectors (e.g., cauliflower mosaic virus, CAMV; tobacco mosaic virus, TMV) or transformed with recombinant plasmid expression vectors (e.g., Ti plasmid) containing the IDGF4 coding sequence; insect cell systems infected with recombinant virus expression vectors (e.g., baculovirus) containing the IDGF4 coding sequence; or animal cell systems infected with recombinant virus expression vectors (e.g., retroviruses, adenovirus, vaccinia virus) containing the IDGF4 coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see e.g., Bitter et al., *Methods in Enzymology* 153:516, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted IDGF4 coding sequence.

In yeast, a number of vectors containing constitutive or inducible promoters may be used. For a review see, *Current Protocols in Molecular Biology*, Vol. 2, 1988, Ed. Ausubel et al., Greene Publish. Assoc. & Wiley Interscience, Ch. 13; Grant et al., Expression and Secretion Vectors for Yeast, in *Methods in Enzymology*, 153:516, 1987; Glover, 1986, *DNA Cloning*, Vol. II, IRL Press, Wash., D.C., Ch. 3; and Bitter, Heterologous Gene Expression in Yeast, *Methods in Enzymology*, 152:673, 1987; and *The Molecular Biology of the Yeast Saccharomyces*, 1982, Eds. Strathem et al., Cold Spring Harbor Press, Vols. I and II. A constitutive yeast promoter such as ADH or LEU2 or an inducible promoter such as GAL may be used (Cloning in Yeast, Ch. 3, R. Rothstein In: *DNA Cloning Vol. 11, A Practical Approach*, Ed. D M Glover, 1986, IRL Press, Wash., D.C.). Alternatively, vectors may be used which promote integration of foreign DNA sequences into the yeast chromosome.

The genetic construct can be designed to provide additional benefits, such as, for example addition of C-terminal or N-terminal amino acid residues that would facilitate purification by trapping on columns or by use of antibodies. All those methodologies are cumulative. For example, a synthetic gene can later be mutagenized. The choice as to the method of producing a particular construct can easily be made by one skilled in the art based on practical considerations: size of the desired peptide, availability and cost of starting materials, etc. All the technologies involved are well established and well known in the art. See, for example, Ausubel et al., *Current Protocols in Molecular Biology*, Volumes 1 and 2 (1987), with supplements, and Maniatis et al., *Molecular Cloning, a Laboratory Manual*, Cold Spring Harbor Laboratory (1989). Yet other technical references are known and easily accessible to one skilled in the art.

Antibodies that bind to IDGF4

In another embodiment, the present invention provides antibodies that bind to IDGF4. Such antibodies are usefull for research and diagnostic tools in the study of cell growth-associated pathologies in general, and specifically the development of more effective diagnostics and therapeutics for wound repair. Such antibodies may be administered alone or contained in a pharmaceutical composition comprising antibodies against IDGF4 and other reagents effective as modulators of cell growth.

Thus, it is envisioned that antibodies of the invention can be used to detect the presence of an antigenic determinant resulting from a cell growth-associated pathology in a subject having, suspected of having or at risk of having, such a pathology.

The term "epitope", as used herein, refers to an antigenic determinant on an antigen, such as a IDGF4 polypeptide, to which the paratope of an antibody, such as an IDGF4-specific antibody, binds. Antigenic determinants usually consist of chemically active surface groupings of molecules, such as amino acids or sugar side chains, and can have specific three-dimensional structural characteristics, as well as specific charge characteristics.

Antibodies which bind to the IDGF4 polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

An antibody suitable for binding to IDGF4 is specific for at least one portion of an extracellular region of the IDGF4 polypeptide, as shown in FIG. 1 (SEQ ID NO:2). For example, one of skill in the art can use the peptides to generate appropriate antibodies of the invention. Antibodies of the invention include polyclonal antibodies, monoclonal antibodies, and fragments of polyclonal and monoclonal antibodies.

The preparation of polyclonal antibodies is well-known to those skilled in the art. See, for example, Green et al., *Production of Polyclonal Antisera, in Immunochemical Piotocols* (Manson, ed.), pages 114 5 (Humana Press 1992); Coligan et al., *Production of Polyclonal Antisera in Rabbits, Rats, Mice and Hamsters*, in *Current Protocols in Immunology*, section 2.4.1 (1992), which are hereby incorporated by reference.

The preparation of monoclonal antibodies likewise is conventional. See, for example, Kohler & Milstein, *Nature*, 256:495 (1975); Coligan et al., sections 2.5.1–2.6.7; and Harlow et al., *Antibodies: A Laboratory Manual*, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g. Coligan et al., sections 2.7.1–2.7.12 and sections 2.9.1–2.9.3; Barnes et al., *Purification of Immunoglobulin G (IgG)*, in *Methods in Molecular Biology*, Vol. 10, pages 79–104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., *Int. J. Cancer*, 46:310 (1990), which are hereby incorporated by reference.

Alternatively, a therapeutically useful anti-IDGF4 antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA*, 86:3833 (1989), which is hereby incorporated in its entirety by reference. Techniques for producing humanized monoclonal antibodies are described, for example, by Jones et al., *Nature*, 321: 522 (1986); Riechmann et al., *Nature*, 332: 323 (1988); Verhoeyen et al., *Science*, 239:1534 (1988); Carter et al., *Proc. Nat'l Acad Sci. USA*, 89:4285 (1992); Sandhu, *Crit. Rev. Biotech.*, 12:437 (1992); and Singer et al., *J. Immunol.*, 150:2844 (1993), which are hereby incorporated by reference.

Antibodies of the invention also may be derived from human antibody fragments isolated from a combinatorial immunoglobulin library. See, for example, Barbas et al, *Methods: A Companion to Methods in Enzymology*, Vol. 2, page 119 (1991); Winter et al., *Ann. Rev. Immunol*. 12: 433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.*, 7:13 (1994); Lonberg et al., *Nature*, 368:856 (1994); and Taylor et al., *Int. Immunol.*, 6:579 (1994), which are hereby incorporated by reference.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and No. 4,331,647, and references contained therein. These patents are hereby incorporated in their entireties by reference. See also Nisonhoff et al., *Arch. Biochem. Biophys.*, 89:230 (1960); Porter, *Biochem. J.*, 73:119 (1959); Edelman et al., *Methods in Enzymology*, Vol. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci USA*, 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology*, Vol. 2, page 97 (1991); Bird et al., *Science*, 242:423 (1988); Ladner et al., U.S. Pat. No. 4,946,778; Pack et al., Bio/Technology, 11:1271 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology*, Vol. 2, page 106 (1991).

When used for immunotherapy, the monoclonal antibodies of the invention that binds to IDGF4 may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., *Science*, 231:148, 1986) and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The labeled or unlabeled monoclonal antibodies of the invention can also be used in combination with therapeutic agents such as those described above. Especially preferred are therapeutic combinations comprising the monoclonal antibody of the invention and immunomodulators and other biological response modifiers.

When the monoclonal antibody of the invention is used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the disorder, the condition of the patient and half-life of the agent.

The dosage ranges for the administration of monoclonal antibodies of the invention are those large enough to produce the desired effect in which the onset symptoms of the cell proliferation-associated pathology are ameliorated. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

It should be understood that all of the above descriptions for IDGF4 pertain equally to other CHRP polypeptides, polynucleotides, antibodies and the like as described herein. For example, the above descriptions relate equally to IDGF1, IDGF2, IDGF3, IDGF4, DS47 gp38k, gp-39, Brp-39, YKL39, YKL40, POSP or homologs or orthologs thereof (e.g., the mammalian equivalent) and should not be construed as relating only to IDGF4 of the invention.

Modulation of Tissue Regeneration

In one embodiment, the invention provides a method for accelerating wound healing in a subject by applying to the wound a therapeutically effective amount of a composition which contains at least one CHRP polypeptide, or biologically functional fragment thereof. Exemplary CHRPs useful in the present method include IDGF1, IDGF2, IDGF3, IDGF4, DS47 gp38k, gp-39, Brp-39, YKL39, YKL40, POSP or homologs or orthologs thereof (e.g., the mammalian equivalent). CHRP polypeptides are valuable as therapeutics in cases in which there is impaired healing of skin wounds or there is a need to augment normal healing mechanisms. Therefore, the term "biologically functional fragment" encompasses any segment of a CHRP polypeptide that retains the ability to promote cell proliferation and/or differentiation.

Agents which promote wound repair can further be included in such compositions to augment wound healing. Such agents include members of the family of growth factors such as insulin-like growth factor (IGF-I), platelet-derived growth factor (PDGF), epidermal growth factor (EGF), connective tissue growth factor (CTGF), transforming growth factor beta (TGF-β), or other members of the TGF-β superfamily, and basic fibroblast growth factor (bFGF). The CHRP compositions are prepared by combining, in any pharmaceutically acceptable carrier substance, e.g., inert gels or liquids, the purified CHRP polypeptides of the invention or related family members.

As used herein, a "therapeutically effective amount" of a composition containing CHRP for use in tissue repair is defined as that amount that is effective in promoting tissue regeneration. Diseases, disorders or ailments modulated by CHRP include tissue regeneration subsequent to traumatic injuries or conditions including arthritis, osteoporosis and other skeletal disorders, and burns. Because these problems are due to a poor growth response of the fibroblasts, stem cells, chondrocytes, osteoblasts or fibroblasts at the site of injury, the addition of an active biologic agent that stimulates or induces growth of these cells is beneficial. The term "induce" or "induction" as used herein, refers to the activation, stimulation, enhancement, initiation and or maintenance of the cellular mechanisms or processes necessary for the formation of any tissue regeneration process or development as described herein.

In another aspect, the invention is useful for revitalizing scar tissue resulting from injuries due to surgical procedures, irradiation, laceration, toxic chemicals, viral infection bacterial infection or burns. The term "scar tissue" means fibrotic or collagenous tissue formed during the healing of a wound or other morbid process. For example, a CHRP of the invention can be included in a controlled release matrix which can be positioned in proximity to damaged tissue thereby promoting regeneration and revascularization of such tissue. The term "controlled release matrix" means any composition which allows the slow release of a bioactive substance which is mixed or admixed therein. The matrix can be a solid composition, a porous material, or a semi-solid, gel or liquid suspension containing bioactive substances. The term "bioactive material" means any composition that will modulate tissue repair when used in accordance with the method of the present invention. The bioactive materials/matrix can be introduced by means of injection, surgery, catheters or any other means suitable for modulating tissue repair.

It is envisioned that the method of the invention can be used to aid wound repair in guided tissue regeneration (GTR) procedures. Such procedures are currently used by those skilled in the medical arts to accelerate wound healing following invasive surgical procedures. Typically, nonresorbable or bioabsorbable membranes are used to accelerate wound healing by promoting the repopulation of the wound area with cells which form the architectural and structural matrix of the tissue. For example, the method of the invention can be used in aiding periodontal tissue regeneration in a human or lower animal by placing a composition containing a bioresorbable polymer, leachable solvent, and CHRP at a site in need of periodontal tissue regeneration such that the composition is effective for aiding tissue regeneration by releasing a therapeutically-effective amount of CHRP at the site.

In another aspect, the invention can be useful for the purposes of promoting tissue growth during the process of tissue engineering. As used herein, "tissue engineering" is defined as the creation, design, and fabrication of biological prosthetic devices, in combination with synthetic or natural materials, for the augmentation or replacement of body tissues and organs. Thus, the present method can be used to augment the design and growth of human tissues outside the body for later implantation in the repair or replacement of diseased tissues. For example, CHRPs may be useful in promoting the growth of skin graft replacements which are used as a therapy in the treatment of burns.

In another aspect of tissue engineering, CHRPs of the present invention can be included in cell-containing or cell-free devices which induce the regeneration of functional human tissues when implanted at a site which requires regeneration. As previously discussed, biomaterial-guided tissue regeneration can be used to promote bone regrowth in, for example, periodontal disease. Thus, CHRPs can be used to promote the growth of reconstituted tissues assembled into three-dimensional configurations at the site of a wound or other tissue in need of such repair.

In another aspect of tissue engineering, CHRPs can be included in external or internal devices containing human tissues designed to replace the function of diseased internal tissues. This approach involves isolating cells from the body, placing them on or within structural matrices, and implanting the new system inside the body or using the system outside the body. The method of the invention can be included in such matrices to promote the growth of tissues contained in the matrices. For example, CHRP can be included in a cell-lined vascular graft to promote the growth of the cells contained in the graft. It is envisioned that the method of the invention can be used to augment tissue repair, regeneration and engineering in products such as cartilage and bone, central nervous system tissues, muscle, liver, and pancreatic islet (insulin-producing) cells.

The present invention further provides a method for modulating female reproductive tract function. Growth factors have been shown to play a role in cyclic mitosis and differentiation of endometrial cellular components, recruitment of macrophages in decidualizing the endometrium, endometrial-trophoblast interactions, early pregnancy maintenance, and endometrial functional regeneration. The term "modulate" as used herein, denotes a modification of an existing condition or biologic state. Modulation of a condition as defined herein, encompasses both an increase or a decrease in the determinants affecting the existing condition. For example, administration of CHRP could be used to augment uterine functions in a condition where the promotion of growth is desired. For example, the uterus may be treated with CHRP to promote the growth and development of placental membranes or endometrial growth. Furthermore, treatment with CHRP may be used to promote and maintain a pregnancy by facilitating endometrial-trophoblast interaction. Alternatively, antagonists to CHRP could be administered to modulate conditions of excessive endometrial growth in which the level of CHRP is excessive in comparison to a normal biologic condition.

Another therapeutic approach included within the invention involves direct administration of reagents or compositions including the CHRP of the invention by any conventional administration technique (for example, but not restricted to, local injection, inhalation, or systemic administration), to a subject with a fibrotic, a sclerotic, or a cell proliferative disorder such as, for example, atherosclerosis or rheumatoid arthritis. Administration of CHRP, as described above, might accelerate wound healing, induce tissue repair or regeneration, or promote the growth and development of the endometrium. The reagent, formulation or composition may also be targeted to specific cells or receptors by any method described herein or by any method known in the art of delivering, targeting and expressing genes encoding CHRP. The actual dosage of reagent, formulation or composition that modulates a fibrotic disorder, a sclerotic disorder, a cell proliferative disorder, atherosclerosis or wound healing depends on many factors, including the size and health of an organism. However, one of ordinary skill in the art can use the following teachings describing the methods and techniques for determining clinical dosages (Spilker B., *Guide to Clinical Studies and Developing Protocols*, Raven Press Books, Ltd., New York, 1984, pp. 7–13, 54–60; Spilker B., *Guide to Clinical Trials*, Raven Press, Ltd., New York, 1991, pp. 93–101; Craig C., and R. Stitzel, eds. , Modern Pharmacology, 2d ed., Little, Brown and Co., Boston, 1986, pp. 127–33; T. Speight, ed., *Avery's Drug Treatment: Principles and Practice of Clinical Pharmacology and Therapeutics*, 3d ed., Williams and Wilkins, Baltimore, 1987, pp. 50–56; R. Tallarida, R. Raffa and P. McGonigle, *Principles in General Pharmacology*, Springer-Verlag, New York, 1988, pp. 18–20) or to determine the appropriate dosage to use.

In yet another embodiment, the invention may provide a method of diagnosing a pathological state in a subject suspected of having pathology characterized by a cell proliferative disorder associated with CHRP, including obtaining a sample suspected of containing CHRP from the subject, determining the level of CHRP in the sample and comparing the level of CHRP in the sample to the level of CHRP in a normal standard sample. Such conditions include but are not restricted to cell proliferative disorders, various fibrotic conditions including scleroderma, arthritis, liver cirrhosis, and uterine fibroids. For example, a sample suspected of containing CHRP is obtained from a subject, the level of CHRP polypeptide is determined and compared with the level of CHRP in a normal tissue sample. The level of CHRP can be determined by immunoassays using anti-CHRP antibodies, for example. Other variations of such assays include radioimmunoassay (RIA), ELISA and immunofluorescence. Alternatively, nucleic acid probes can be used to detect and quantitate CHRP polypeptide mRNA for the same purpose.

In another embodiment, the invention may provide a method for ameliorating a cell proliferative disorder associated with CHRP, including treating a subject having the disorder, at the site of the disorder, with a composition which regulates CHRP production or activity. The term "ameliorate" denotes a lessening of the detrimental effect of the disease-inducing response in the patient receiving therapy. Where the disease is due to an overgrowth of cells, an antagonist of CHRP polypeptide may be effective in decreasing the amount of available CHRP. Such an antagonist may be a CHRP specific antibody or functional fragments thereof (e.g., Fab, F(ab')2).

The term "cell proliferative disorder", as used herein, refers to a condition characterized by abnormal cell growth. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations may be transformed, tumorigenic, malignant or metastatic cells, but can include normal cells as well. For example, CHRP may be involved in a pathological condition by inducing a proliferative lesion in the intimal layer of an arterial wall, resulting in atherosclerosis. CHRP polypeptide inhibitors or antagonists of the invention would be useful in interfering with the in vivo activity of CHRP associated with atherosclerosis. CHRP polypeptide antagonists are also useful in treating other disorders associated with an overgrowth of connective tissues, such as various fibrotic conditions, including scleroderma, arthritis and liver cirrhosis.

In yet another embodiment, the invention may provide a method of treating a subject having a cell proliferative disorder associated with abnormal CHRP gene expression. The method includes administering to a subject having the disorder a therapeutically effective amount of an agent which modulates CHRP gene expression, thereby treating the disorder. The term "modulate" refers to inhibition or suppression of CHRP expression when CHRP is overexpressed, and induction of expression when CHRP is underexpressed. The term "therapeutically effective" means that amount of CHRP agent which is effective in reducing the symptoms of the CHRP associated cell proliferative disorder.

An agent which modulates CHRP gene expression may be a polynucleotide for example. The polynucleotide may be an antisense, a triplex agent, or a ribozyme, as described above. For example, an antisense may be directed to the structural gene region or to the promoter region of CHRP.

When a cell proliferative disorder is associated with abnormal expression of CHRP, a therapeutic approach which directly interferes with the translation of CHRP messages into protein is possible. For example, antisense nucleic acid or ribozymes could be used to bind to the CHRP mRNA or to cleave it. Antisense RNA or DNA molecules bind specifically with a targeted gene's RNA message, interrupting the expression of that gene's protein product. The antisense binds to the messenger RNA forming a double stranded molecule which cannot be translated by the cell. Antisense oligonucleotides of about 15–25 nucleotides are preferred since they are easily synthesized and have an inhibitory effect just like antisense RNA molecules. In addition, chemically reactive groups, such as iron-linked ethylenediaminetetraacetic acid (EDTA-Fe) can be attached to an antisense oligonucleotide, causing cleavage of the RNA at the site of hybridization. These and other uses of antisense methods to inhibit the in vitro translation of genes are well known in the art (Marcus-Sakura, *Anal. Biochem.*, 172:289,1988).

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target CHRP producing cell. The use of antisense methods to inhibit the in vitro translation of genes is well known in the art (Marcus-Sakura, *Anal. Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1:227, 1991; Helene, *Anticancer Drug Design*, 6:569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

These and other uses of antisense methods to inhibit the in vivo translation of genes are well known in the art (e.g., De Mesmaeker, et al., *Curr. Opin. Struct. Biol.*, 5:343, 1995; Gewirtz, A. M., et al., *Proc. Natl. Acad. Sci U.S.A.*, 93:3161, 1996b; Stein, C. A., *Chem. and Biol.* 3:319, 1996).

Delivery of antisense, triplex agents, ribozymes, competitive inhibitors and the like can be achieved using a recombinant expression vector such as a chimeric virus or a colloidal dispersion system. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a polynucleotide sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to $\Psi 2$, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for polynucleotides a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are usefull as delivery vehicles in vitro and in vivo. It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors which will allow the targeted delivery system to find and "home in" on the desired cells. A ligand may be any compound of interest which will bind to another compound, such as a receptor.

The therapeutic agents useful in the method of the invention can be administered parenterally by injection or by gradual perfusion over time. Administration may be intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

Pharmaceutical Compositions

It is envisioned that methods of the present invention can be used to treat pathologies associated with cell proliferative disorders. Therefore, the present invention encompasses methods for ameliorating a cell proliferative disorder associated with CHRP, including treating a subject having the disorder, at the site of the disorder, with a CHRP reactive agent. Exemplary CHRPs useful in the present method include IDGF1, IDGF2, IDGF3, IDGF4, DS47 gp38k, gp-39, Brp-39, YKL39, YKL40, POSP or homologs or orthologs thereof (e g., the mammalian equivalent). Generally, the terms "treating", "treatment" and the like are used herein to mean obtaining a desired pharmacologic and/or physiologic effect. The effect may be prophylactic in terms of completely or partially preventing a disease or sign or symptom thereof, and/or may be therapeutic in terms of a partial or complete cure for an infection or disease and/or adverse effect attributable to the infection or disease. "Treating" as used herein covers any treatment of, or prevention of, an infection or disease in a mammal, particularly a human, and includes:

(a) preventing the disease from occurring in a subject that may be predisposed to the disease, but has not yet been diagnosed as having it;

(b) inhibiting the disease, i.e., arresting its development; or (c) relieving or ameliorating the disease, i.e., cause regression of the disease.

Thus, the invention includes various pharmaceutical compositions useful for ameliorating symptoms attributable to a cell proliferative disorder. The pharmaceutical compositions according to the invention are prepared by bringing an antibody against CHRP, a polypeptide or peptide derivative of CHRP, a CHRP mimetic, or a CHRP-binding agent according to the present invention into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences*, 15th ed. Easton: Mack Publishing Co., 1405–1412, 1461–1487 (1975) and *The National Formulary XIV.*, 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's *The Pharmacological Basis for Therapeutics* (7th ed.).

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Langer, *Science*, 249: 1527, (1990); Gilman et al. (eds.) (1990), each of which is herein incorporated by reference.

In one embodiment, the invention provides a pharmaceutical composition useful for administering a CHRP polypeptide, or nucleic acid encoding a CHRP polypeptide, to a subject in need of such treatment. "Administering" the pharmaceutical composition of the present invention may be accomplished by any means known to the skilled artisan. Preferably a "subject" refers to a mammal, most preferably a human.

The CHRP protein or antibody can be administered parenterally by injection, rapid infusion, nasopharyngeal absorption, dermal absorption, and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water.

Screening Assay for Compounds that Affect CHRPs

In another embodiment, the invention provides a method for identifying a compound which modulates CHRP expression or activity including incubating components comprising the compound and a CHRP polypeptide, or a recombinant cell expressing a CHRP polypeptide, under conditions sufficient to allow the components to interact and determining the affect of the compound on the expression or activity of the gene or polypeptide, respectively. Exemplary CHRPs useful in the present method include IDGF1, IDGF2, IDGF3, IDGF4, DS47 gp38k, gp-39, Brp-39, YKL39, YKL40, POSP or homologs or orthologs thereof (e.g., the mammalian equivalent). The term "affect", as used herein, encompasses any means by which CHRP gene expression or protein activity can be modulated. Such compounds can include, for example, polypeptides, peptidomimetics, chemical compounds and biologic agents as described below.

Incubating includes conditions which allow contact between the test compound and CHRP, a cell expressing CHRP or nucleic acid encoding CHRP. Contacting includes in solution and in solid phase. The test ligand(s)/compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

Thus, the method of the invention includes combinatorial chemistry methods for identifying chemical compounds that bind to CHRP or affect CHRP expression or activity. By providing for the production of large amounts of a CHRP, one can identify ligands or substrates that bind to, modulate, affect the expression of, or mimic the action of a CHRP. For example, a polypeptide may have biological activity associated with the wild-type protein, or may have a loss of function mutation due to a point mutation in the coding sequence, substitution, insertion, deletion and scanning mutations.

Areas of investigation are the development of therapeutic treatments. The screening identifies agents that provide modulation of CHRP function in targeted organisms. Of particular interest are screening assays for agents that have a low toxicity for humans. A wide variety of assays may be used for this purpose, including labeled in vitro protein-protein binding assays, protein-DNA binding assays, electrophoretic mobility shift assays, immunoassays for protein binding, and the like. The purified protein may also be used for determination of three-dimensional crystal structure, which can be used for modeling intermolecular interactions and transcriptional regulation, for example. The term "agent" as used herein describes any molecule, e.g. protein or pharmaceutical, with the capability of altering or mimicking the physiological function or expression of a CHRP. Generally, a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above finctional groups. Candidate agents are also found among biomolecules including, but not limited to: peptides, saccharides, fatty acids, steroids, purines, pyrimidines, derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification and amidification to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors and anti-microbial agents may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Detection of CHRP in Vivo and in Vitro

In a further embodiment, the invention provides a method of detecting a cell growth-associated disorder in a subject including contacting a cell component containing CHRP with a reagent which binds to the cell component. Exemplary CHRPs useful in the present method include IDGF1, IDGF2, IDGF3, IDGF4, DS47 gp38k, gp-39, Brp-39, YKL39, YKL40, POSP or homologs or orthologs thereof (e.g., the mammalian equivalent). The cell component can be nucleic acid, such as DNA or RNA, or it can be protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzymne. Those of ordinary skill in the art will know of other labels suitable for binding to an antibody or nucleic acid probe, or will be able to ascertain such, using routine experimentation.

For purposes of the invention, an antibody or nucleic acid probe specific for CHRP may be used to detect the presence of CHRP polypeptide (using antibody) or polynucleotide (using nucleic acid probe) in biological fluids or tissues. Any specimen containing a detectable amount of CHRP antigen or polynucleotide can be used. For example, specimens of this invention include blood, urine, cerebrospinal fluid, synovial fluid or tissue of endothelial origin.

Another technique which may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Alternatively, CHRP polypeptide can be used to detect antibodies to CHRP polypeptide in a specimen. The CHRP of the invention is particularly suited for use in immunoassays in which it can be utilized in liquid phase or bound to a solid phase carrier. In addition, CHRP used in these assays can be detectably labeled in various ways.

Examples of immunoassays which can utilize the CHRP of the invention are competitive and noncompetitive immunoassays in either a direct or indirect format. Examples of such immunoassays are the radioimmunoassay (RIA), the sandwich (immunometric assay) and the Western blot assay. Detection of antibodies which bind to the CHRP of the invention can be done utilizing immunoassays which run in either the forward, reverse, or simultaneous modes, including immunohistochemical assays on physiological samples. The concentration of CHRP which is used will vary depending on the type of immunoassay and nature of the detectable label which is used. However, regardless of the type of immunoassay which is used, the concentration of CHRP utilized can be readily determined by one of ordinary skill in the art using routine experimentation.

The CHRP of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding CHRP or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to CHRP of the invention may be present in various biological fluids and tissues. Any sample containing a detectable amount of antibodies to CHRP can be used. Typically, a sample is a liquid such as urine, saliva, cerebrospinal fluid, blood, serum and the like, or a solid or semi-solid such as tissue, feces and the like.

The monoclonal antibodies of the invention, directed toward CHRP, are also useful for the in vivo detection of antigen. The detectably labeled monoclonal antibody is given in a dose which is diagnostically effective. The term "diagnostically effective" means that the amount of detectably labeled monoclonal antibody is administered in sufficient quantity to enable detection of CHRP antigen for which the monoclonal antibodies are specific.

The concentration of detectably labeled monoclonal antibody which is administered should be sufficient such that the binding to those cells, body fluid, or tissue having CHRP is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the subject. Such dosages may vary, for example, depending on whether multiple injections are given, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 key range, which may be readily detected by conventional gamma cameras.

For in vivo diagnosis, radioisotopes may be bound to immunoglobulin either directly or indirectly by using an intermediate finctional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used to monitor the course of amelioration of a cell proliferation-associated disorder. Thus, by measuring the increase or decrease of CHRP polypeptide present in various body fluids or tissues, it would be possible to determine whether a particular therapeutic regiment aimed at ameliorating the disorder is effective.

In another embodiment, nucleic acid probes can be used to identify CHRP nucleic acid from a specimen obtained from a subject suspected of having a cell growth-associated pathology. Examples of specimens from which nucleic acid sequence encoding CHRP can be derived include insect, human, swine, porcine, feline, canine, equine, murine, cervine, caprine, lupine, leporidine and bovine species. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.* 9:879, 1981).

In an embodiment of the invention, purified nucleic acid fragments containing intervening sequences or oligonucleotide sequences of 10–50 base pairs are radioactively labeled. The labeled preparations are used to probe nucleic acid from a specimen by the Southern hybridization technique. Nucleotide fragments from a specimen, before or after amplification, are separated into fragments of different molecular masses by gel electrophoresis and transferred to filters that bind nucleic acid. After exposure to the labeled probe, which will hybridize to nucleotide fragments containing target nucleic acid sequences, binding of the radioactive probe to target nucleic acid fragments is identified by autoradiography (see *Genetic Engineering*, 1, ed. Robert Williamson, Academic Press, (1981), 72–81). Alternatively, nucleic acid from the specimen can be bound directly to filters to which the radioactive probe selectively attaches by binding nucleic acids having the sequence of interest. Specific sequences and the degree of binding is quantitated by directly counting the radioactive emissions.

Where the target nucleic acid is not amplified, detection using an appropriate hybridization probe may be performed directly on the separated nucleic acid. In those instances where the target nucleic acid is amplified, detection with the appropriate hybridization probe would be performed after amplification.

The probes of the present invention can be used for examining the distribution of the specific fragments detected, as well as the quantitative (relative) degree of binding of the probe for determining the occurrence of specific strongly binding (hybridizing) sequences, thus indicating the likelihood for an subject having or predisposed to having increased muscle mass.

For the most part, the probe will be detectably labeled with an atom or inorganic radical, most commonly using radionuclides, but also heavy metals can be used. Conveniently, a radioactive label may be employed. Radioactive labels include $^{32}$P, $^{125}$I, $^{3}$H, $^{14}$C, $^{111}$In, $^{99m}$Tc, or the like. Any radioactive label may be employed which provides for an adequate signal and has sufficient half-life. Other labels include ligands, which can serve as a specific binding pair member for a labeled ligand, and the like. A wide variety of labels routinely employed in immunoassays can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an a $^{32}$P-DNTP or terminal phosphate hydrolysis with alkaline phosphatase followed by labeling with radioactive $^{32}$P employing $^{32}$P-NTP and T4 polynucleotide kinase. Alternatively, nucleotides can be synthesized where one or more of the elements present are replaced with a radioactive isotope, e.g., hydrogen with tritium. If desired, complementary labeled strands can be used as probes to enhance the concentration of hybridized label.

Where other radionucleotide labels are involved, various linking groups can be employed. A terminal hydroxyl can be esterified, with inorganic acids, e.g., $^{32}$P phosphate, or $^{14}$C organic acids, or else esterified to provide linking groups to the label. Alternatively, intermediate bases may be substituted with activatable linidng groups that can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodanine and its derivatives, dansyl, umbelliferone, and so forth. Chemiluminescers include luciferin, and 2,3-dihydrophthalazinediones (e.g., luminol).

The probe can be employed for hybridizing to a nucleotide sequence affixed to a water insoluble porous support. Depending upon the source of the nucleic acid, the manner in which the nucleic acid is affixed to the support may vary. Those of ordinary skill in the art know, or can easily ascertain, different supports that can be used in the method of the invention.

The nucleic acid from a specimen can be cloned and then spotted or spread onto a filter to provide a plurality of individual portions (plaques). The filter is an inert porous solid support, e.g., nitrocellulose. Any cells (or phage) present in the specimen are treated to liberate their nucleic acid. The lysing and denaturation of nucleic acid, as well as the subsequent washings, can be achieved with an appropriate solution for a sufficient time to lyse the cells and denature the nucleic acid. For lysing, chemical lysing will conveniently be employed, as described previously for the lysis buffer. Other denaturation agents include elevated temperatures, organic reagents, e.g., alcohols, amides, amines, ureas, phenols and sulfoxides or certain inorganic ions, e.g., thiocyanate and perchlorate.

After denaturation, the filter is washed in an aqueous buffered solution, such as Tris, generally at a pH of about 6 to 8, usually 7. One or more washings may be involved, conveniently using the same procedure as employed for the lysing and denaturation. After the lysing, denaturing, and washes have been accomplished, the nucleic acid spotted filter is dried at an elevated temperature, generally from about 50° C. to 70° C. Under this procedure, the nucleic acid is fixed in position and can be assayed with the probe when convenient.

Pre-hybridization may be accomplished by incubating the filter with the hybridization solution without the probe at a mildly elevated temperature for a sufficient time to thoroughly wet the filter. Various hybridization solutions may be employed, comprising from about 20% to 60% volume, preferably 30%, of an inert polar organic solvent. A common hybridization solution employs about 50% formamide, about 0.5 to 1M sodium chloride, about 0.05 to 0.1M sodium citrate, about 0.05 to 0.2% sodium dodecylsulfate, and minor amounts of EDTA, ficoll (about 300–500 kDa), polyvinylpyrrolidone, (about 250–500 kDa) and serum albumin. Also included in the hybridization solution will generally be from about 0.5 to 5 mg/ml of sonicated denatured DNA, e.g., calf thymus of salmon sperm; and optionally from about 0.5 to 2% wt/vol glycine. Other additives may also be included, such as dextran sulfate of from about 100 to 1,000 kDa and in an amount of from about 8 to 15 weight percent of the hybridization solution.

The particular hybridization technique is not essential to the invention. Other hybridization techniques are described by Gall and Pardue, (*Proc. Natl. Acad. Sci.* 63:378, 1969); and John, et al., (*Nature*, 223:582, 1969). As improvements are made in hybridization techniques they can readily be applied in the method of the invention.

The amount of labeled probe present in the hybridization solution will vary widely, depending upon the nature of the label, the amount of the labeled probe that can reasonably bind to the filter, and the stringency of the hybridization. Generally, substantial excess over stoichiometric concentrations of the probe will be employed to enhance the rate of binding of the probe to the fixed target nucleic acid.

In nucleic acid hybridization reactions, the conditions used to achieve a particular level of stringency will vary, depending on the nature of the nucleic acids being hybridized. For example, the length, degree of complementarity, nucleotide sequence compound (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

After the filter has been contacted with a hybridization solution at a moderate temperature for a period of time sufficient to allow hybridization to occur, the filter is then introduced into a second solution having analogous concentrations of sodium chloride, sodium citrate and sodium dodecylsulfate as provided in the hybridization solution. The time the filter is maintained in the second solution may vary from five minutes to three hours or more. The second solution determines the stringency, dissolving cross duplexes and short complementary sequences. After rinsing the filter at room temperature with dilute sodium citrate-sodium chloride solution, the filter may now be assayed for the presence of duplexes in accordance with the nature of the label. Where the label is radioactive, the filter is dried and exposed to X-ray film.

The label may also comprise a fluorescent moiety that can then be probed with a specific fluorescent antibody. Horseradish peroxidase enzyme can be conjugated to the antibody to catalyze a chemiluminescent reaction. Production of light can then be seen on rapid exposure to film.

Growth Promotion of Cultured Cells by CHRP

In another embodiment, the invention provides a method for supplementing a culture system with CHRP in order to promote the production and maintenance of an insect or mammalian cell or cell line. Exemplary CHRPs useful in the present method include IDGF1, IDGF2, IDGF3, IDGF4, DS47 gp38k, gp-39, Brp-39, YKL39, YKL40, POSP or homologs or orthologs thereof (e.g., the mammalian equivalent). The media used in the culture system is preferably a commonly used liquid tissue culture media The media can be free of serum and supplemented with various defined components which allow the insect or mammalian cell to proliferate. CHRP is usefull for supplementing any culture media well known in the art, such as Grace's insect cell media or Dulbecco's minimal essential media (DMEM), which contains appropriate amino acids, vitamins, inorganic salts, a buffering agent, and an energy source. Purified molecules, which include hormones, growth factors, transport proteins, trace elements, vitamins, and substratum-modifying factors are added to the media to replace biological fluids.

Kits for Detection of CHRP

The materials for use in the method of the invention are ideally suited for the preparation of a kit. Such a kit may comprise a carrier means being compartmentalized to receive one or more container means such as vials, tubes, and the like, each of the container means comprising one of the separate elements to be used in the method. For example, one of the container means may comprise a CHRP binding reagent, such as an antibody or nucleic acid. A second container may further comprise CHRP polypeptide. Exemplary CHRPs useful in the present method include IDGF1, IDGF2, IDGF3, IDGF4, DS47 gp38k, gp-39, Brp-39, YKL39, YKL40, POSP or homologs or orthologs thereof (e.g., the mammalian equivalent). The constituents may be present in liquid or lyophilized form, as desired.

One of the container means may comprise a probe which is or can be detectably labeled. Such probe may be an antibody or nucleotide specific for a target protein, or fragments thereof, or a target nucleic acid, or fragment thereof, respectively, wherein the target is indicative, or correlates with, the presence of CHRP. For example, oligonucleotide probes of the present invention can be included in a kit and used for examining the presence of CHRP nucleic acid, as well as the quantitative (relative) degree of binding of the probe for determining the occurrence of specific strongly binding (hybridizing) sequences, thus indicating the likelihood for an subject having a cell growth-associated pathology.

The kit may also contain a container comprising a reporter-means, such as a biotin-binding protein, such as avidin or streptavidin, bound to a reporter molecule, such as an enzymatic, fluorescent, or radionucleotide label to identify the detectably labeled oligonucleotide probe.

Where the kit utilizes nucleic acid hybridization to detect the target nucleic acid, the kit may also have containers containing nucleotide(s) for amplification of the target nucleic acid sequence. When it is desirable to amplify the target nucleic acid sequence, such as a CHRP nucleic acid sequence, this can be accomplished using oligonucleotide(s) that are primers for amplification. These oligonucleotide primers are based upon identification of the flanking regions contiguous with the target nucleotide sequence.

The kit may also include a container containing antibodies which bind to a target protein, or fragments thereof. Thus, it is envisioned that antibodies which bind to CHRP, or fragments thereof, can be included in a kit.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Growth of C1.8+ Cells in Supplement-Free (SFM) or Conditioned (CM) Media

The wing-disc cell line C1.8+ (Peel, et al., *Roux's Arch. Develop. Biol.*, 202:23, 1992) was cultured in Shields and Sang's M3 medium (Shields, et al., *J. Embryol. Exp. Morphol.*, 23:53, 1970) supplemented with 2% fetal bovine serum (Sigma, F3018), 0.125 IU/ml bovine insulin (Sigma, I1882) and 2.5% fly extract (Currie, et al., *Development*, 102:805, 1988). The cells were replated on 60 mm plastic dishes at a density of $0.5 \times 10^6$ cells/ml, and allowed to proliferate for 3–4 days in the same medium until they became subconfluent. The subconfluent cultures were then washed three times with PBS or SFM. In order to ensure thorough washing, they were incubated in the third washing medium for 1 hour. Conditioned medium (CM) was prepared by incubating the cells in SFM medium for 4 days. The CM was collected after removal of cell debris by centrifugation and stored at 4° C. Alternatively, CM was prepared by culturing confluent cells that had been inoculated at high density ($4 \times 10^6$ cells/ml).

C1.8+ cultured in supplement-free Shields and Sang M3 medium (SFM), (ie., medium lacking fly extract, serum and insulin) became flattened within a few hours after plating, but did not form pseudopodia. Further, the cells failed to incorporate bromodeoxyuridine (BrdU), decreased in number by about 50% over a four-day period and underwent apoptosis as indicated by time-lapse video microscopy. However, the cell line showed a remarkable change of properties when cultured in conditioned medium (CM) that had been prepared by growing C1.8+ cells to subconfluence in complete medium and then incubating them in SFM for four days. Within a few hours after plating in this conditioned SFM, the cells became bipolar, then developed pseudopodia and elongated. After one day of culture, the cells formed aggregates and showed enhanced motility. The cells did not fragment but rather doubled in number in two days. Cell number was estimated quantitatively using the MTT (3-(4,5-dimethylthiazol-2-yl)-2,5-diphenyltetrazolium bromide) method (Denizot, et al., *J. Immunological Methods*, 89:271, 1986).

In addition, cells grown in CM showed a BrdU labeling index of 35.1+9.9% (mean+S.D.) as compared to a BrdU labeling index of 0% for those grown in SFM. CM prepared from confluent cultures was also effective for enhancing cell survival, but it had a weaker effect on cell growth than that from subconfluent cultures. These results suggest that C1.8+ cells secrete factors into the culture medium to stimulate their own growth.

EXAMPLE 2

Isolation of Cell Growth-Promoting Activity

Anion Exchange Chromatography

Figure 3A:
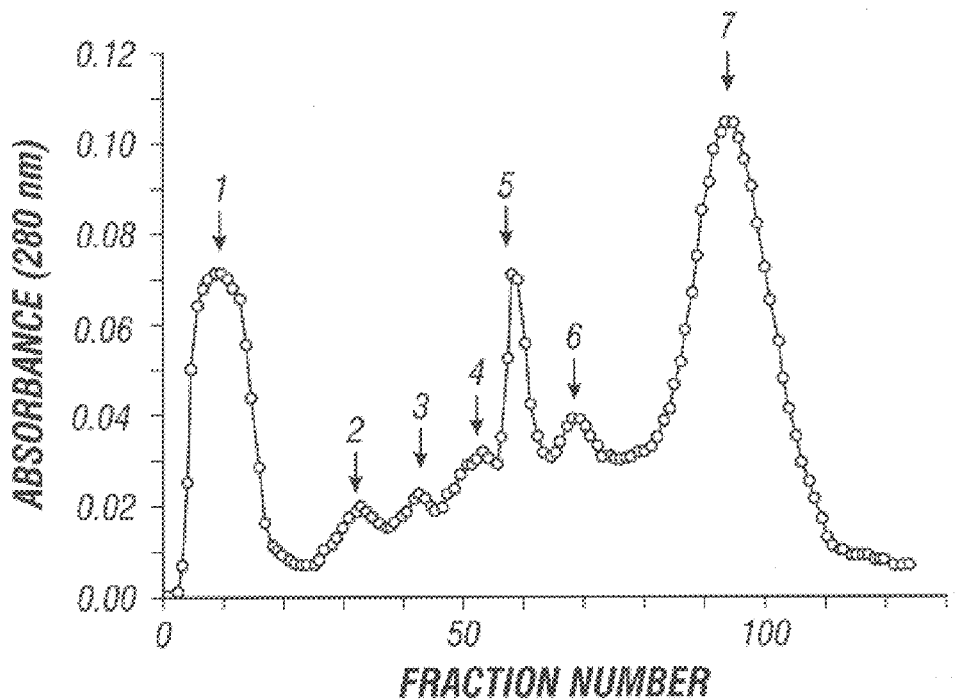
FIG. 3A shows a protein elution profile following fractionation of conditioned medium (CM) by anion exchange chromatography. The fifth peak demonstrated the highest cell growth-promoting activity of the seven eluted protein peaks.

The CM was dialyzed against 20 mM phosphate buffer (pH 8.0) and passed through an anion exchange column (2.5×10 cm) of DE 52 (Whatman) equilibrated with the same buffer. The column was eluted with a linear gradient of 0–0.5 M NaCl in the same buffer (4 ml/6 min/tube). The eluate was monitored for absorbance at 280 nm which generated seven separate peaks of eluted proteins in seven fractions (FIG. 3A). Fractions 4, 5 and 6 had a positive effect on cell survival, and fraction 5 showed the highest growth-promoting activity. Fraction 5 improved cell survival at a minimal concentration of 0.4 μg/ml, and stimulated cell growth at a minimal concentration of 0.8 μg/ml. The addition of insulin enhanced these effects while insulin alone failed to show any growth-promoting activity.

Gel Filtration HPLC

Figure 3B:
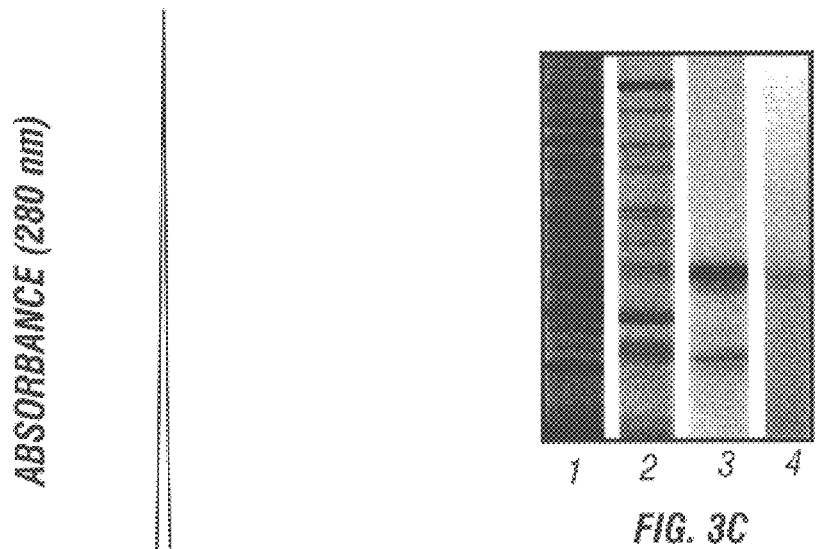
FIG. 3B shows an elution profile of fraction 5 (isolated by anion exchange chromatography, FIG. 3A) following gel filtration by high performance liquid chromatography (HPLC). The primary peak (indicated by an arrow) demonstrated cell growth-promoting activity.
Figure 3C:
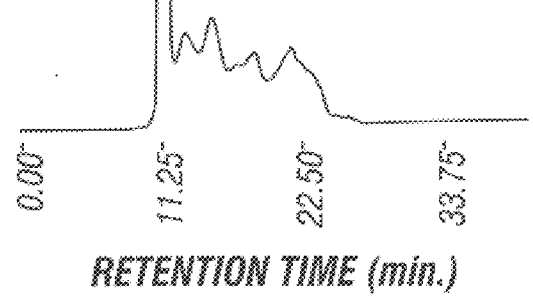
FIG. 3C shows fractionated samples of CM on a sodium dodecyl sulfate-polyacrylamide gel (SDS-PAGE). The gels were silver stained following separation by electrophoresis. Lane 1 shows the proteins present in a crude extract. Lane 2 shows the proteins present in fraction 5 identified in FIG. 3A following anion exchange chromatography. Lane 3 shows the proteins present in the primary peak identified in FIG. 3B following gel filtration HPLC. Lane 4 shows a 50 kDa polypeptide purified following preparative electrophoresis of the primary peak identified in FIG. 3B.

Fraction 5 was further purified by gel filtration HPLC (high performance liquid chromatography). A prepacked gel filtration column (Shodex, KW-803) was connected with a Jasco's liquid chromatographic system consisting of an 801-SC system controller, an 880-PU pump and an 875-UV detector (Japan Spectroscopic Co. Ltd). The column was eluted with 50 mM phosphate buffer containing 0.5 M NaCl and 0.05% brij-35 at a flow rate of 0.5 ml/min. Following elution, most of the growth promoting activity was recovered in the primary peak (FIG. 3B, arrow). The active fractions constituting the primary peak showed a prominent 50 kDa polypeptide by sodium dodecyl sulfate polyacrylamide gel electrophoresis (SDS-PAGE) (FIG. 3C, lanes 1–3). SDS-PAGE was carried out on 10% polyacrylamide gel containing 0.1% SDS in 0.375 M Tris-HCl (pH 8.8). Following electrophoresis, the gel was silver stained (Boehringer) and the amount of protein determined (Lowry, et al., *J. Biol. Chem.*, 193:265, 1951).

Preparative Gel Electrophoresis

The 50 kDa polypeptide was further purified by preparative gel electrophoresis (FIG. 3C, lane 4). Preparative electrophoresis was carried out in the presence or absence of sodium dodecyl sulfate (SDS), using a Model 491 Prep Cell (Bio-Rad, Inc.). After isolation, the 50 kDa polypeptide was blotted onto PVDF membrane using a sample cartridge (ProSpin, Applied Biosystems). The membrane was washed thoroughly and applied to a gas-phase protein microsequencer (470/900A, Applied Biosystems) to obtain the N-terminal amino acid sequence of the protein.

EXAMPLE 3

N-terminal Microsequencing of the Isolated 50 kDa Protein

Figures 4A, 4B:
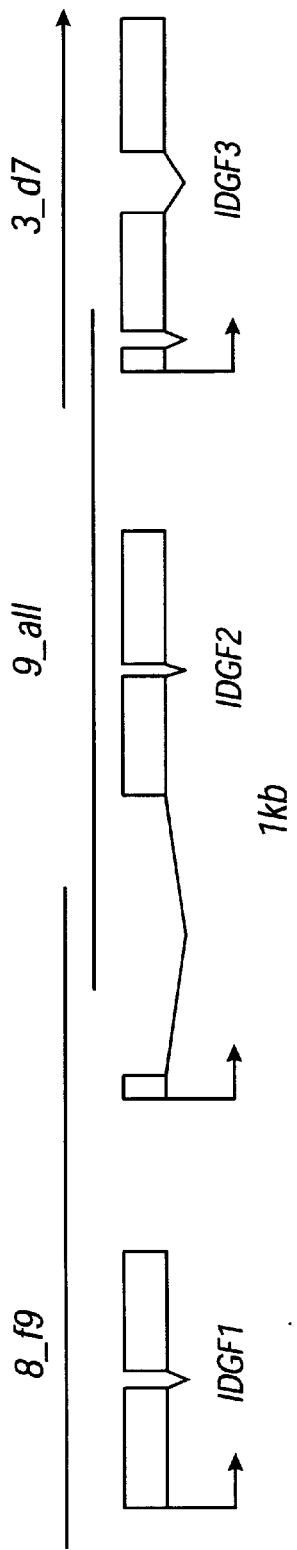

Microsequencing of the purified 50 kDa protein from the N-terminus provided a sequence of 32 amino acids (FIG. 4B, "Micro"). Although this sequence did not completely match any protein sequences in available databases, it closely resembled (47% identity over 32 residues) the sequence of the 452 amino acid (47 kDa) glycoprotein DS47 (Kirkpatrick, et al., *Gene*, 153:147, 1995). This protein is abundantly secreted from a Drosophila embryo-derived cell line (S2), and is produced in vivo by the fat body and hemocytes and secreted into the hemolymph. It is encoded by the gene Chit at 53D, but no mutations in this gene have been reported.

The N-terminal sequence of the 50 kDa polypeptide shows an even closer match to those predicted from three putative genes in genomic DNA subclones 8 f9, 9 a1 1 and 3 d7, all within a 9 kb interval in P1 clone DS02780 from chromosome 2, cytological region 36A2-4 (FIG. 4A). The amino acid sequences predicted by these three putative transcripts are about 50% identical to each other and to the sequence of DS47 (FIG. 4B), suggesting the existence of a gene family with at least four members. All three predicted sequences contain an N-terminal signal sequence, and a single consensus motif for N-inked glycosylation as reported for DS47 at amino acid residue 233 (Kirkpatrick, et al., Gene, 153:147, 1995). They are closely related to (15–25% identity) but distinct from, chitinases (poly N-acetylglucosaminidases), the enzymes that catalyze the hydrolysis of the beta-1,4-N-acetyl-D-glucosamine linkages in chitin polymers of the arthropod cuticle (Hakala, et al., J. Biol. Chem., 268:25803, 1993). The three predicted proteins identified through by microsequence are referred to as imaginal disc growth factors 1, 2 and 3 (IDGF1, IDGF2 and IDGF3) corresponding to the open reading frames in 8 9f, 9 a1 1 and 3 d7, respectively. Although the microsequence does not match exactly any of these three sequences, the microsequence data can be entirely explained by assuming that our purified fraction contains a mixture of at least IDGF1 and IDGF3 (FIG. 4B).

Unlike chitinases, IDGFs probably do not bind chitin since they lack the cysteine-rich chitin recognition or binding domain (B. Iseli, et al., Plant Physiol., 103:221, 1993). This makes it unlikely that they promote growth by acting as lectins. Instead, they may function synergistically with Drosophila insulin or a Drosophila insulin-like molecule. Insulin promotes growth of Drosophila cell primary cultures (Echalier, Academic Press, San Diego, 1997) and is necessary for the growth of imaginal disc cells (Cullen, et al., Tissue Cell, 23:29 1991). The gene encoding the Drosophila insulin receptor (DIR) is expressed in imaginal discs (Garofalo, et al., Molec. Cell. Biol., 8:1638, 1988), and in larvae homozygous for receptor mutations the growth of imaginal discs is inhibited (Chen, et al., Endocrinology, 137:846, 1996). The receptor activity appears to be required in the embryonic epidermis and central nervous system (Fernandez, et al., EMBO J., 14:3373, 1995). DIR binds mammalian insulin with high affinity but fails to bind to insulin-like growth factor I and II (IGF I and II) or epidermal growth factor (EGF) (Petruzzelli, et al., J. Biol Chem. 260:16072, 1985). Consistent with this finding, when mixed with IDGFs bovine insulin at 50 ng/ml was effective, whereas IGF I was ineffective in inducing growth of C1.8+ cells.

The expression of IDGF genes in the fat body is consistent with previous reports showing that the fat body produces mitogenic factors. For example, the conditioning of medium by fat body, or coculture with fat body, allows growth of imaginal discs in vitro by cell proliferation (Davis, et al., Science 196:1, 1977). These conditions also allow regeneration and transdetermination of imaginal disc fragments, events generally thought to require cell proliferation, in vitro. The fat body may therefore be an important source of growth factors like IDGF that support peripheral tissue growth during insect development.

The IDGFs belong to a family that includes several mammalian secreted glycoproteins of ill-defined function, none of which have been previously identified as a growth factor. The family includes a heparin-binding glycoprotein (gp38k; 22% identical to IDGF3) produced during differentiation of vascular smooth muscle cells (Shackelton, et al., J. Biol. Chem., 270:13076, 1995); a major secretory product (HCgp-39; 21% identical to IDGF3) of articular chondrocytes and synovial cells from patients with arthritis (Hakala, et al., J. Biol. Chem. 268:25803, 1993); and a protein (Brp-39; 19% identical to IDGF3) secreted by certain murine mammary tumors (Morrison, et al., Oncogene, 9:3417, 1994). Closely related proteins (YKL39 and YKL40; 17% and 21% identical to IDGF3) accumulate in chondrocyte conditioned medium (Hu, et al., J. Biol. Chem., 271:19415, 1996), and others are secreted by the mammalian oviduct (Buhi, et al., Biol. Reprod., 55:1305, 1996).

EXAMPLE 4

Identification and Isolation of IDGF4 cDNA

Generation of IDGF Fragments by PCR

On the basis of the genomic sequence information, PCR primers were designed for each IDGF gene. The fragments were amplified by PCR from genomic DNA and an imaginal disc cDNA library. Amplification was initiated for one cycle at 94° C. for 1 min, followed by 26 cycles at 94° C. for 30 sec, 55° C. for 1 min and 72° C. for 2 min. The following primers used for PCR amplification:

IDGF1F: 5' AACGAATTCGATTTGGCCCTGCAGTTC 3' (SEQ ID NO:3)

IDGF1R: 5' CAGTGCAGGATCCACGGAAGTCATC 3' (SEQ ID NO:4)

IDGF2F: 5' TTGGCTGAATTCAAAGTGAGCGCCGCT 3' (SEQ ID NO:5)

IDGF2R: 5' GCACTCGGATCCTTGATCAGTGCAGT 3' (SEQ ID NO:6)

IDGF3F: 5' AAGCTGCCTCGAGCTTAGTCTGCTAC 3' (SEQ ID NO:7)

IDGF3R: 5' CATTGGGAAGCTTAGTCAGACTGAGC 3' (SEQ ID NO:8)

The fragments resulting from the amplification process were digested with appropriate restriction enzymes, subcloned into pBluescript SK- (Stratagene) and used for further analysis.

Screening a Library with IDGF Polynucleotide Fragments

An imaginal disc cDNA library was screened using the IDGF polynucleotide fragments obtained from PCR amplification described above. cDNA fragments for each IDGF were $^{32}$P radiolabeled by random priming (Stratagene) and used for screening over 500,000 clones of an imaginal disc and larval cDNA library. Hybridization reactions was performed in 0.5 M Sodium phosphate (pH 7.2), 7% SDS and 1 mM EDTA at 65° C. Filters were washed in 0.2×SSC (1×, 150 mM NaCl and 15 mM sodium citrate) and 0.2% SDS at 65° C. After three rounds of screening, positive clones were isolated and subcloned into pBluescript. The nucleotide sequences of IDGF genes on both strands were determined using a ThermoSequenase radiolabeled terminator cycle sequence kit (Amersham). Nucleotide and protein sequences were analyzed using MACAW (Schuler, et al., Proteins Struct. Funct. Genet., 9:180, 1991). cDNA clones were obtained for IDGF1, 2 and 3. The DNA sequences of these clones matched the sequences predicted from the genomic sequence using several gene finder programs. Database searching revealed six closely related EST clones encoding a new protein subsequently named IDGF4.

Isolation of IDGF4 cDNA

The following PCR primers were used to amplify a polynucleotide fragment of IDGF4:

IDGF4F: 5' TTTGGCCATTGGTCAGAATTCCCG 3' (SEQ ID NO:9)

IDGF4R: 5' TGCTCTCCAGCAGGGTCAGATACT 3' (SEQ ID NO:10)

The fragment was used as a probe to isolate IDGF4 cDNA from a larval cDNA library. The predicted IDGF4 protein is 46–50% identical to IDGF1–3. However, the gene is not linked to the other IDGF1–3 genes, but is localized on the X chromosome in band 9A. The only other member of this family reported from insects, aside from authentic chitinases, is the Haemocyte Aggregation Inhibiting Protein from the tobacco hornworm *Manduca sexta* (Kanost, et al., *Arch. Insect Biochem. Physiol.*, 27:123, 1994).

EXAMPLE 5

Developmental Expression of IDGFs

IDGF PCR fragments were used as probes to examine the developmental expression of IDGF1–3 by Northern blot analysis. Each IDGF was expressed at all tested stages but most heavily in mid-larval stages when imaginal discs undergo growth by cell proliferation. IDGF1 mRNA showed weaker expression than IDGF2 and 3. The tissue expression pattern of IDGF genes was determined in embryos and larvae by in situ hybridization to whole mounts using digoxigenin-labeled probes. Sense and antisense digoxigenin-labeled RNA were transcribed from linearized pBluescript containing each IDGF cDNA using T3 and T7 RNA polymerase (Promega) and a digoxigenin labeling mixture (Boehringer Mannheim). Dechorionated embryos and partially dissected larvae were fixed and hybridized with RNA probes in 50% formamide, 5×SSC, 250 mg/ml salmon-sperm DNA, 50 mg/ml heparin and 0.1% Tween20 at 55° C. (Theisen, et al., *Development*, 122:3939, 1996). Signals were detected by anti-digoxigenin-AP Fab fragments (Boehringer Mannheim). There were no detectable signals from sense RNA probes. IDGF genes are abundantly expressed in the embryonic amnioserosa, and in the fat body of both embryo and larva. There is also a low level of expression in imaginal discs and proliferating cells in the optic lobes.

EXAMPLE 6

Expression and Isolation of IDGF Polypeptides

Recombinant IDGF1 and IDGF2 were prepared using a baculovirus protein expression system. A full-length cDNA for each IDGF was inserted into the multicloning site of the baculovirus transfer vector, pBlueBac-His2 (InVitrogen) which provides a His tag for affinity purification. The transfer vector and linearized baculovirus DNA were co-transfected overnight into the host cell, sf-9. For lipofection, Cellfectin (Gibco, 10362-028) was diluted 1:50 with SF-900II (Gibco, 10902-013). After screening by LacZ expression and PCR, recombinant baculovirus were purified from positive plaques, cloned and amplified (Webb, et al., *Techn.*, 2:173, 1990). Three days after transfection with high-titer virus, cells were sonicated in the lysis buffer (20 mM Tris, 0.1 M NaCl, 6 M urea, pH 8.0). His-tagged recombinant proteins were bound to a metal-affinity resin (Clontech) and eluted with 50 mM imidazole. In order to remove the tag, the recombinant proteins were treated with 10 U/ml enterokinase (Biozyme, EK2B) in 70 mM sodium succinate buffer (pH 5.6) for 2 hours at 25° C. The enzyme was heat-inactivated and the protein solution was dialyzed against PBS (pH 7.6) before bioassay.

Figure 2B:
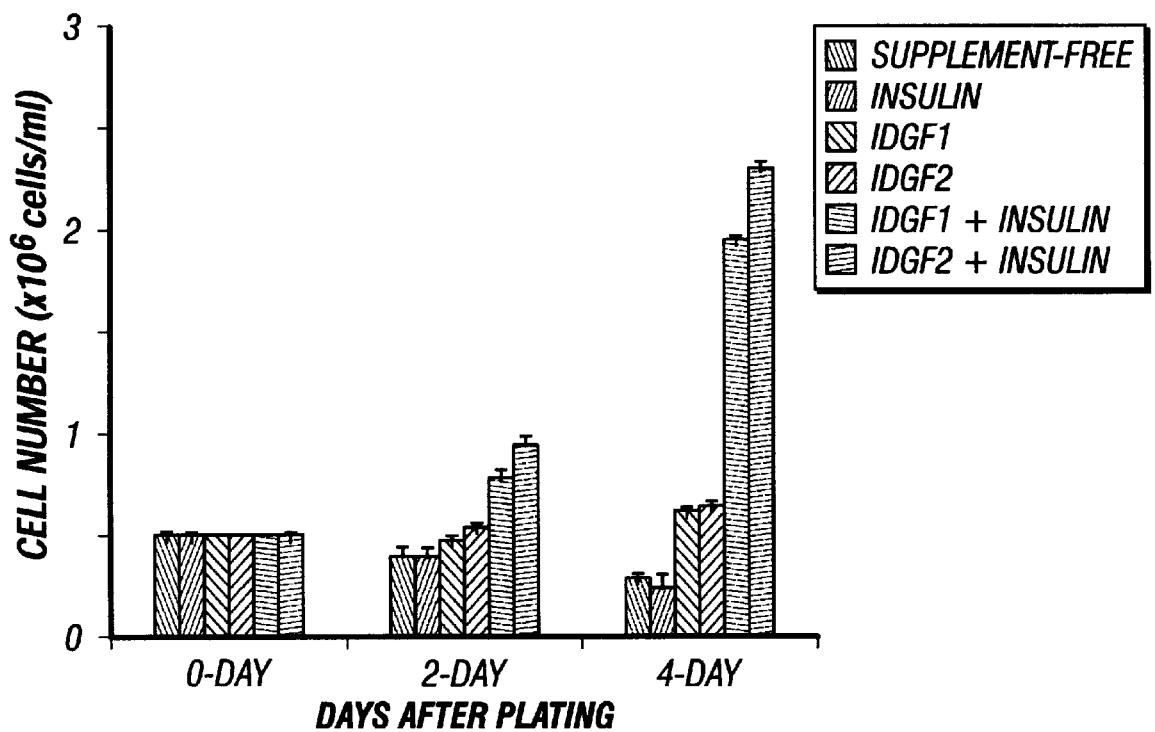
FIG. 2B shows a bar graph indicating the effect of recombinant IDGFs on proliferation of the imaginal disc cell line C1.8+. C1.8+ cells were plated at $0.5 \times 10^6$ cells/ml in 24-well plates and allowed to proliferate for four days in SFM supplemented with IDGF 1 or IDGF2 (0.2 µg/ml) in the presence and absence of insulin (0.125 U/ml). The results show strong molecular cooperation between IDGFs and insulin in promoting cell growth. The bars represent the standard deviation.

The expressed and isolated IDGF proteins promoted cell growth at concentrations above 0.2 µg/ml, depending upon dosage (FIG. 2B). At higher concentrations, the growth promoting activity was much higher than that of fraction 5 after anion exchange chromatography. One day post-plating, cells produced lamellipodia and elongated gradually, similarly to those treated with fraction 5. IDGF1 and IDGF2 carrying N-terminal His tags were inactive in the growth assessment assays, indicating that the activity depends on intact IDGF structure, especially the N-terminal conformation of the proteins. Insulin (0.125 IU/ml) enhanced the effect of IDGF1 and IDGF2 on cell growth and elongation (FIG. 2B), but did not show either activity alone.

It will be apparent to those skilled in the art that various modifications and variations can be made to the compounds and processes of this invention. Thus, it is intended that the present invention cover such modifications and variations, provided they come within the scope of the appended claims and their equivalents. Accordingly, the invention is limited only by the following claims.

---

What is claimed is:

1. A substantially purified IDGF4 polypeptide having an amino acid sequence as set forth in SEQ ID NO:2.

* * * * *

SEQUENCE LISTING

<160> NUMBER OF SEQ ID NOS: 16

<210> SEQ ID NO 1
<211> LENGTH: 1500
<212> TYPE: DNA
<213> ORGANISM: Drosophila melanogaster
<220> FEATURE:
<221> NAME/KEY: CDS
<222> LOCATION: (9)...(1334)

<400> SEQUENCE: 1

```
ggcacgag atg aag ctc tac gcc ctg ttc tcc ctt ctg gtg gga tct ttg      50
         Met Lys Leu Tyr Ala Leu Phe Ser Leu Leu Val Gly Ser Leu
           1               5                  10 gcc att ggt cag att tcc gcc gcc gga tct cat cat cta ctt tgt tac       98
Ala Ile Gly Gln Ile Ser Ala Ala Gly Ser His His Leu Leu Cys Tyr
 15                  20                  25                  30 tat gac ggc aac agt ttt gtc cgc gag ggc ctc tcc aag ctg atc cta      146
Tyr Asp Gly Asn Ser Phe Val Arg Glu Gly Leu Ser Lys Leu Ile Leu
                 35                  40                  45
```

-continued

| | |
|---|---:|
| acc gat ctg gag ccc gcc ctg cag tac tgc acc cat ctg gtc tac gga<br>Thr Asp Leu Glu Pro Ala Leu Gln Tyr Cys Thr His Leu Val Tyr Gly<br>                 50                      55                  60 | 194 |
| tat gcc ggc att aat ccc tcg agc aac aag ctg gtc agc aac aat gag<br>Tyr Ala Gly Ile Asn Pro Ser Ser Asn Lys Leu Val Ser Asn Asn Glu<br>     65                      70                      75 | 242 |
| aaa ccg gac ctg gat ctg ggc agc agc ctg ttc cgc cag gtg acc gga<br>Lys Pro Asp Leu Asp Leu Gly Ser Ser Leu Phe Arg Gln Val Thr Gly<br> 80                      85                      90 | 290 |
| ttg aag cgc aag tac cca gcc ctc aag gtc ctg ctt agc gtg ggt ggc<br>Leu Lys Arg Lys Tyr Pro Ala Leu Lys Val Leu Leu Ser Val Gly Gly<br>  95                    100               105             110 | 338 |
| gac aag gac acc gtg gat cca gag aac aac aag tat ctg acc ctg ctg<br>Asp Lys Asp Thr Val Asp Pro Glu Asn Asn Lys Tyr Leu Thr Leu Leu<br>                115                   120               125 | 386 |
| gag agc agc aat gcc agg att ccg ttc atc aac agt gct cac tcg ctg<br>Glu Ser Ser Asn Ala Arg Ile Pro Phe Ile Asn Ser Ala His Ser Leu<br>              130                  135               140 | 434 |
| gtg aag acc tac ggt ttc gat ggc ctc gat ctc ggc tgg cag ttc ccc<br>Val Lys Thr Tyr Gly Phe Asp Gly Leu Asp Leu Gly Trp Gln Phe Pro<br>           145                   150               155 | 482 |
| aag aat aag cca aag aag gtg cac ggc agc att ggc aag ttc tgg aag<br>Lys Asn Lys Pro Lys Lys Val His Gly Ser Ile Gly Lys Phe Trp Lys<br>         160                   165              170 | 530 |
| gga ttc aag aag atc ttc agc ggt gat cat ctc gtc gac gag aag gcc<br>Gly Phe Lys Lys Ile Phe Ser Gly Asp His Leu Val Asp Glu Lys Ala<br>175                    180               185              190 | 578 |
| gag gag cac aag gag gcc ttc acc gcc ctg gtt cgc gaa ctg aag aac<br>Glu Glu His Lys Glu Ala Phe Thr Ala Leu Val Arg Glu Leu Lys Asn<br>              195                  200              205 | 626 |
| gcc ttc cgt ccc gat ggc tac atc ctg ggt ctc agt gtc ctg ccc aat<br>Ala Phe Arg Pro Asp Gly Tyr Ile Leu Gly Leu Ser Val Leu Pro Asn<br>           210                  215               220 | 674 |
| gtg aac tct tcg ctg ttc ttc gat gtg ccc gct att atc aat aac ttg<br>Val Asn Ser Ser Leu Phe Phe Asp Val Pro Ala Ile Ile Asn Asn Leu<br>         225                   230               235 | 722 |
| gac tac gtg aac ctg cac acc tac gac ttc cag acc ccc gag cgc aac<br>Asp Tyr Val Asn Leu His Thr Tyr Asp Phe Gln Thr Pro Glu Arg Asn<br>240                    245               250 | 770 |
| aac gag gtg gcc gac ttc ccg gca ccg atc tac gag ctg aac gag cgc<br>Asn Glu Val Ala Asp Phe Pro Ala Pro Ile Tyr Glu Leu Asn Glu Arg<br>255                    260               265              270 | 818 |
| aat ccg gag ttc aat gtc aac tac cag gtg aaa tac tgg acc gga aac<br>Asn Pro Glu Phe Asn Val Asn Tyr Gln Val Lys Tyr Trp Thr Gly Asn<br>           275                   280               285 | 866 |
| cgt gct ccg gcc gct aag att aac gtg ggc att gcc acc tat gga cgt<br>Arg Ala Pro Ala Ala Lys Ile Asn Val Gly Ile Ala Thr Tyr Gly Arg<br>         290                   295              300 | 914 |
| gcc tgg aaa ttg acc aag gat tcg gga ctg act gga ctt cca ccg gtt<br>Ala Trp Lys Leu Thr Lys Asp Ser Gly Leu Thr Gly Leu Pro Pro Val<br>      305                   310               315 | 962 |
| gcc gag gct gat ggt gtg gct cct gcc gga acc cag acc cag ata ccc<br>Ala Glu Ala Asp Gly Val Ala Pro Ala Gly Thr Gln Thr Gln Ile Pro<br>320                    325               330 | 1010 |
| gga ctt ctt agc tgg cca gag gtg tgc gcc aag ctc cca aat ccc gcc<br>Gly Leu Leu Ser Trp Pro Glu Val Cys Ala Lys Leu Pro Asn Pro Ala<br>335                    340               345              350 | 1058 |
| aat cag cat ctg aag ggc gcc gat ggt ccg ctg cga aag gtt ggt gat<br>Asn Gln His Leu Lys Gly Ala Asp Gly Pro Leu Arg Lys Val Gly Asp | 1106 |

```
                     355                  360                  365
ccg acc aag cgc ttt gga agc tat gcc tac ccg tcc gcc gac gac agc      1154
Pro Thr Lys Arg Phe Gly Ser Tyr Ala Tyr Pro Ser Ala Asp Asp Ser
            370                 375                 380 ggt gaa aac gga gtc tgg gtg ggc tac gag gat ccc gat acg gcg gcc      1202
Gly Glu Asn Gly Val Trp Val Gly Tyr Glu Asp Pro Asp Thr Ala Ala
        385                 390                 395 atc aag gcg gag tat gtt aag cgc gag ggt ctc ggc ggc att gct gtt      1250
Ile Lys Ala Glu Tyr Val Lys Arg Glu Gly Leu Gly Gly Ile Ala Val
    400                 405                 410 gtc gat ctg agc ttc gat gac ttc cgc ggc ggc tgc act ggc cac gac      1298
Val Asp Leu Ser Phe Asp Asp Phe Arg Gly Gly Cys Thr Gly His Asp
415                 420                 425                 430 aag ttc ccc atc ctg cgc cag gtc aag agc aag ttg tagagctcct           1344
Lys Phe Pro Ile Leu Arg Gln Val Lys Ser Lys Leu
                435                 440 catcctcctg attcttttcc ggaacggaag aacaaacgtg ttttatttg ccccgctgtt     1404 tttttatat gtaattgact caacgcaaac ctgtgtaaac gcgaaatgca aatttaaass     1464
aatataacat tgacaccaaa aaaaaaaaaa aaaaaa                              1500

<210> SEQ ID NO 2
<211> LENGTH: 442
<212> TYPE: PRT
<213> ORGANISM: Drosophila melanogaster

<400> SEQUENCE: 2

Met Lys Leu Tyr Ala Leu Phe Ser Leu Leu Val Gly Ser Leu Ala Ile
1               5                   10                  15

Gly Gln Ile Ser Ala Ala Gly Ser His His Leu Leu Cys Tyr Tyr Asp
            20                  25                  30

Gly Asn Ser Phe Val Arg Glu Gly Leu Ser Lys Leu Ile Leu Thr Asp
        35                  40                  45

Leu Glu Pro Ala Leu Gln Tyr Cys Thr His Leu Val Tyr Gly Tyr Ala
    50                  55                  60

Gly Ile Asn Pro Ser Ser Asn Lys Leu Val Ser Asn Glu Lys Pro
65                  70                  75                  80

Asp Leu Asp Leu Gly Ser Ser Leu Phe Arg Gln Val Thr Gly Leu Lys
                85                  90                  95

Arg Lys Tyr Pro Ala Leu Lys Val Leu Leu Ser Val Gly Gly Asp Lys
            100                 105                 110

Asp Thr Val Asp Pro Glu Asn Asn Lys Tyr Leu Thr Leu Leu Glu Ser
        115                 120                 125

Ser Asn Ala Arg Ile Pro Phe Ile Asn Ser Ala His Ser Leu Val Lys
    130                 135                 140

Thr Tyr Gly Phe Asp Gly Leu Asp Leu Gly Trp Gln Phe Pro Lys Asn
145                 150                 155                 160

Lys Pro Lys Lys Val His Gly Ser Ile Gly Lys Phe Trp Lys Gly Phe
                165                 170                 175

Lys Lys Ile Phe Ser Gly Asp His Leu Val Asp Glu Lys Ala Glu Glu
            180                 185                 190

His Lys Glu Ala Phe Thr Ala Leu Val Arg Glu Leu Lys Asn Ala Phe
        195                 200                 205

Arg Pro Asp Gly Tyr Ile Leu Gly Leu Ser Val Leu Pro Asn Val Asn
    210                 215                 220

Ser Ser Leu Phe Phe Asp Val Pro Ala Ile Ile Asn Asn Leu Asp Tyr
```

```
               225                 230                 235                 240

Val Asn Leu His Thr Tyr Asp Phe Gln Thr Pro Glu Arg Asn Asn Glu
                        245                 250                 255

Val Ala Asp Phe Pro Ala Pro Ile Tyr Glu Leu Asn Glu Arg Asn Pro
                260                 265                 270

Glu Phe Asn Val Asn Tyr Gln Val Lys Tyr Trp Thr Gly Asn Arg Ala
                275                 280                 285

Pro Ala Ala Lys Ile Asn Val Gly Ile Ala Thr Tyr Gly Arg Ala Trp
                290                 295                 300

Lys Leu Thr Lys Asp Ser Gly Leu Thr Gly Leu Pro Pro Val Ala Glu
    305                 310                 315                 320

Ala Asp Gly Val Ala Pro Ala Gly Thr Gln Thr Gln Ile Pro Gly Leu
                        325                 330                 335

Leu Ser Trp Pro Glu Val Cys Ala Lys Leu Pro Asn Pro Ala Asn Gln
                340                 345                 350

His Leu Lys Gly Ala Asp Gly Pro Leu Arg Lys Val Gly Asp Pro Thr
                355                 360                 365

Lys Arg Phe Gly Ser Tyr Ala Tyr Pro Ser Ala Asp Asp Ser Gly Glu
                370                 375                 380

Asn Gly Val Trp Val Gly Tyr Glu Asp Pro Asp Thr Ala Ala Ile Lys
    385                 390                 395                 400

Ala Glu Tyr Val Lys Arg Glu Gly Leu Gly Gly Ile Ala Val Val Asp
                        405                 410                 415

Leu Ser Phe Asp Asp Phe Arg Gly Gly Cys Thr Gly His Asp Lys Phe
                        420                 425                 430

Pro Ile Leu Arg Gln Val Lys Ser Lys Leu
                435                 440

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide for PCR

<400> SEQUENCE: 3
aacgaattcg atttggccct gcagttc                                          27

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide for PCR

<400> SEQUENCE: 4
cagtgcagga tccacggaag tcatc                                            25

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide for PCR

<400> SEQUENCE: 5
ttggctgaat tcaaagtgag cgccgct                                          27

<210> SEQ ID NO 6
```

<211> LENGTH: 26
<212> TYPE: DNA
<213> ORGANISM: Artificial Sequence
<220> FEATURE:
<223> OTHER INFORMATION: Oligonucleotide for PCR

<400> SEQUENCE: 6
gcactcggat ccttgatcag tgcagt                                    26

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide for PCR

<400> SEQUENCE: 7
aagctgcctc gagcttagtc tgctac                                    26

<210> SEQ ID NO 8
<211> LENGTH: 26
<212> TYPE: DNA
<213> ORGANISM: Artificial Sequence
<220> FEATURE:
<223> OTHER INFORMATION: Oligonucleotide for PCR

<400> SEQUENCE: 8
cattgggaag cttagtcaga ctgagc                                    26

<210> SEQ ID NO 9
<211> LENGTH: 24
<212> TYPE: DNA
<213> ORGANISM: Artificial Sequence
<220> FEATURE:
<223> OTHER INFORMATION: Oligonucleotide for PCR

<400> SEQUENCE: 9
tttggccatt ggtcagaatt cccg                                      24

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide for PCR

<400> SEQUENCE: 10
tgctctccag cagggtcaga tact                                      24

<210> SEQ ID NO 11
<211> LENGTH: 32
<212> TYPE: PRT
<213> ORGANISM: Drosophila melanogaster
<220> FEATURE:
<221> NAME/KEY: VARIANT
<222> LOCATION: (1)...(32)
<223> OTHER INFORMATION: Xaa = Any Amino Acid

<400> SEQUENCE: 11

Ala Pro Asn Leu Val Lys Tyr Tyr Asp Ser Gln Xaa Tyr Gln Arg Gln
 1               5                  10                  15

Gly Leu Ala Lys Met Xaa Met Ile Glu Leu Xaa Leu Ala Leu Gln Phe
            20                  25                  30

<210> SEQ ID NO 12
<211> LENGTH: 428

-continued

```
<212> TYPE: PRT
<213> ORGANISM: Drosophila melanogaster

<400> SEQUENCE: 12

Met Arg Phe Gln Leu Phe Tyr Ile Leu Gly Leu Leu Ser Val Thr Ser
 1               5                  10                  15

Leu Thr His Ala Ala Ser Asn Leu Ile Cys Tyr Tyr Asp Ser Asn Ser
             20                  25                  30

Tyr Leu Arg Gln Gly Leu Ala Lys Met His Thr Asn Glu Leu Asp Leu
         35                  40                  45

Ala Leu Gln Phe Cys Thr His Leu Val Tyr Gly Tyr Ala Gly Leu Lys
     50                  55                  60

Ser Gly Thr Leu Glu Leu Phe Ser Leu Asn Val Asp Leu Asp Met Phe
 65                  70                  75                  80

Tyr Tyr Lys Asp Ile Thr Ala Leu Arg Gln Lys Phe Pro Gln Leu Lys
                 85                  90                  95

Ile Leu Leu Ser Val Gly Gly Asp Arg Asp Val Asp Glu Ala His Pro
            100                 105                 110

Asn Lys Tyr Val Glu Leu Leu Glu Asn Arg Thr Ala Gln Gln Asn Phe
        115                 120                 125

Ile Asp Ser Ser Met Ile Leu Leu Lys Arg Asn Gly Phe Asp Gly Leu
    130                 135                 140

Asp Leu Ala Phe Gln Leu Pro Arg Asn Lys Pro Arg Lys Val His Gly
145                 150                 155                 160

Ser Leu Gly Ser Tyr Trp Lys Ser Phe Lys Lys Leu Phe Thr Gly Asp
                165                 170                 175

Phe Val Val Asp Pro Gln Ala Glu Glu His Lys Ser Gln Phe Thr Asp
            180                 185                 190

Leu Val Gly Asn Ile Lys Asn Ala Phe Arg Ser Ala Asn Leu Met Leu
        195                 200                 205

Ser Leu Thr Val Leu Pro Asn Val Asn Ser Thr Trp Tyr Phe Asp Val
    210                 215                 220

Pro Lys Leu His Pro Gln Phe Asp Tyr Ile Asn Leu Ala Ala Phe Asp
225                 230                 235                 240

Phe Leu Thr Pro Leu Arg Asn Pro Glu Glu Ala Asp Phe Thr Ala Pro
                245                 250                 255

Ile Phe Phe Gln Asp Glu Gln Asn Arg Leu Pro His Leu Asn Val Glu
            260                 265                 270

Phe Gln Ile Asn Tyr Trp Leu Gln Asn His Cys Pro Gly Gln Lys Leu
        275                 280                 285

Asn Leu Gly Ile Ala Ser Tyr Gly Arg Ala Trp Lys Leu Ser Lys Gly
    290                 295                 300

Ser Gly Leu Ser Gly Ala Pro Ile Val His Glu Thr Cys Gly Val Ala
305                 310                 315                 320

Pro Gly Gly Gly Leu Leu Ser Trp Pro Glu Ile Cys Ser Lys Leu Ser
                325                 330                 335

Gln Asn Ala Ser Ala Gln Tyr Arg Gly Glu Leu Ala Pro Leu Arg Lys
            340                 345                 350

Val Thr Asp Leu Thr Gln Lys Tyr Gly Asn Tyr Ala Leu Arg Pro Ala
        355                 360                 365

Asp Asp Asn Gly Asp Phe Gly Val Trp Leu Ser Phe Asp Pro Asp
    370                 375                 380

Phe Ala Gly Ile Lys Ala Val Tyr Ala Lys Gly Lys Gly Leu Gly Gly
385                 390                 395                 400
```

-continued

```
Ile Ala Leu Phe Asp Leu Ser Tyr Asp Asp Phe Arg Gly Leu Cys Thr
                405                 410                 415
Gly Gln Lys Tyr Pro Ile Leu Arg Ser Ile Lys Tyr
            420                 425

<210> SEQ ID NO 13
<211> LENGTH: 440
<212> TYPE: PRT
<213> ORGANISM: Drosophila melanogaster

<400> SEQUENCE: 13

Met Lys Ala Trp Ile Trp Phe Thr Phe Val Ala Cys Leu Phe Ala Ala
 1               5                  10                  15
Ser Thr Glu Ala Ala Ser Asn Leu Val Cys Tyr Tyr Asp Ser Ser Ser
             20                  25                  30
Tyr Thr Arg Glu Gly Glu Gly Lys Leu Leu Asn Pro Asp Leu Glu Ile
         35                  40                  45
Ala Leu Gln Phe Cys Ser His Leu Val Tyr Gly Tyr Ala Gly Leu Arg
     50                  55                  60
Gly Glu Asn Leu Gln Ala Tyr Ser Met Asn Glu Asn Leu Asp Ile Tyr
 65                  70                  75                  80
Lys His Gln Phe Ser Glu Val Thr Ser Leu Lys Arg Lys Tyr Pro His
                 85                  90                  95
Leu Lys Val Leu Leu Ser Val Gly Gly Asp His Asp Ile Asp Pro Asp
            100                 105                 110
His Pro Asn Lys Tyr Ile Asp Leu Leu Glu Gly Glu Lys Val Arg Gln
        115                 120                 125
Ile Gly Phe Ile Arg Ser Ala Tyr Asp Leu Val Lys Thr Tyr Gly Phe
    130                 135                 140
Asp Gly Leu Asp Leu Ala Tyr Gln Phe Pro Lys Asn Lys Pro Arg Lys
145                 150                 155                 160
Val His Gly Asp Leu Gly Leu Ala Trp Lys Ser Ile Lys Lys Leu Phe
                165                 170                 175
Thr Gly Asp Phe Ile Val Asp Pro His Ala Ala Leu His Lys Glu Gln
            180                 185                 190
Phe Thr Ala Leu Val Arg Asp Val Lys Asp Ser Leu Arg Ala Asp Gly
        195                 200                 205
Phe Leu Leu Ser Leu Thr Val Leu Pro Asn Val Asn Ser Thr Trp Tyr
    210                 215                 220
Phe Asp Ile Pro Ala Leu Asn Gly Leu Val Asp Phe Val Asn Leu Ala
225                 230                 235                 240
Thr Phe Asp Phe Leu Thr Pro Ala Arg Asn Pro Glu Glu Ala Asp Tyr
                245                 250                 255
Ser Ala Pro Ile Tyr His Pro Asp Gly Ser Lys Asp Arg Leu Ala His
            260                 265                 270
Leu Asn Ala Asp Phe Gln Val Glu Tyr Trp Leu Ser Gln Gly Phe Pro
        275                 280                 285
Ser Asn Lys Ile Asn Leu Gly Val Ala Thr Tyr Gly Asn Ala Trp Lys
    290                 295                 300
Leu Thr Lys Asp Ser Gly Leu Glu Gly Val Pro Val Val Pro Glu Thr
305                 310                 315                 320
Ser Gly Pro Ala Pro Glu Gly Phe Gln Ser Gln Lys Pro Gly Leu Leu
                325                 330                 335
Ser Tyr Ala Glu Ile Cys Gly Lys Leu Ser Asn Pro Gln Asn Gln Phe
```

-continued

```
                  340                 345                 350
Leu Lys Gly Asn Glu Ser Pro Leu Arg Arg Val Ser Asp Pro Thr Lys
            355                 360                 365

Arg Phe Gly Gly Ile Ala Tyr Arg Pro Val Asp Gly Gln Ile Thr Glu
        370                 375                 380

Gly Ile Trp Val Ser Tyr Asp Pro Asp Ser Ala Ser Asn Lys Ala
385                 390                 395                 400

Ala Tyr Ala Arg Val Lys Asn Leu Gly Val Ala Leu Phe Asp Leu
                405                 410                 415

Ser Tyr Asp Asp Phe Arg Gly Gln Cys Ser Gly Asp Lys Tyr Pro Ile
                420                 425                 430

Leu Arg Ala Ile Lys Tyr Arg Leu
            435                 440

<210> SEQ ID NO 14
<211> LENGTH: 441
<212> TYPE: PRT
<213> ORGANISM: Drosophila melanogaster

<400> SEQUENCE: 14

Met Thr Gly Ser Leu Trp Leu Ser Leu Ala Leu Ser Leu Ala Val Leu
1               5                   10                  15

Ala Gln Phe Lys Val Ser Ala Ala Pro Asn Leu Val Cys Phe Tyr Asp
            20                  25                  30

Ser Gln Gly Ser Gln Arg Gln Gly Leu Ala Gln Phe Ser Met Ile Asp
        35                  40                  45

Ile Glu Leu Ala Leu Gln Phe Cys Thr His Leu Val Tyr Gly Tyr Ala
    50                  55                  60

Gly Val Asn Ala Asp Asn Tyr Glu Met Gln Ser Ile Asn Lys Arg Leu
65                  70                  75                  80

Asp Leu Glu Gln Arg His Leu Ala Gln Ile Thr Ser Met Lys Glu Arg
                85                  90                  95

Tyr Pro His Ile Lys Phe Leu Ser Val Gly Gly Asp Ala Asp Thr
            100                 105                 110

Asn Glu Gly Asn Gln Tyr Ile Lys Leu Leu Glu Ser Gly Gln Gln Gly
        115                 120                 125

His Arg Arg Phe Ile Glu Ser Ala Arg Asp Leu Val Arg Arg Tyr Asn
    130                 135                 140

Phe Asp Gly Leu Asp Leu Ala Leu Gln Leu Pro Arg Asn Lys Pro Arg
145                 150                 155                 160

Lys Val His Gly Asp Val Gly Ser Ala Trp Lys Ser Phe Lys Lys Phe
                165                 170                 175

Phe Thr Gly Asp Phe Ile Val Asp Thr Glu Ser Glu Thr His Lys Gly
            180                 185                 190

Gln Val Thr Ala Leu Ile Lys Asp Leu Ser Ala Ala Leu Lys Gln Asn
        195                 200                 205

Asp Leu Leu Leu Ser Leu Thr Val Leu Pro Asn Val Asn Ser Ser Trp
    210                 215                 220

Tyr Tyr Asp Ala Pro Ser Ile Ala Pro Ser Leu Asp Phe Ile Asn Leu
225                 230                 235                 240

Gly Thr Phe Asp Phe Leu Thr Pro Gln Arg Asn Pro Glu Glu Ala Asp
                245                 250                 255

Phe Ser Ala Pro Thr Tyr Glu Ala Val Gly Gln Asn Arg Leu Gly His
            260                 265                 270
```

```
Tyr Asn Leu Asn Phe Gln Met Glu His Trp Leu Leu Gln Arg Val Pro
            275                 280                 285

Ala Asn Lys Ile Asn Ile Gly Ile Ala Thr Tyr Gly Arg Ser Trp Lys
        290                 295                 300

Met Ser Lys Asp Ser Gly Asp Ser Gly Met Pro Val Val Pro Ser Thr
305                 310                 315                 320

Gln Gly Pro Ala Pro Ala Gly Pro Gln Ser Lys Gln Glu Gly Leu Leu
                325                 330                 335

Asn Trp Ala Glu Ile Cys Ser Leu Met Pro Asn Pro Ser Asn Thr Asn
            340                 345                 350

Ala Arg Gly Pro Asn Ala Pro Val Lys Arg Val Val Asp Pro Thr Lys
        355                 360                 365

Arg Tyr Gly Ser Tyr Ala Phe Arg Ala Ala Asp Glu Asn Gly Asp His
    370                 375                 380

Gly Leu Trp Ile Ser Tyr Asp Asp Pro Asp Ser Ala Ser Ser Lys Ala
385                 390                 395                 400

Met Tyr Ala Arg Ala Arg Asn Leu Gly Gly Val Ala Leu Phe Asp Leu
                405                 410                 415

Thr Gln Asp Asp Phe Arg Gly Gln Cys Thr Asn Asp Arg Phe Pro Met
            420                 425                 430

Leu Arg Ala Ile Lys Tyr Arg Leu Leu
        435                 440

<210> SEQ ID NO 15
<211> LENGTH: 452
<212> TYPE: PRT
<213> ORGANISM: Drosophila melanogaster

<400> SEQUENCE: 15

Met Ile Ile Lys Ala Leu Ala Ile Val Ser Leu Cys Leu Ala Ser Ile
1               5                   10                  15

Gln Ala Ser Lys Val Gly Ala Pro Gln Leu Pro Lys Lys His Leu Val
            20                  25                  30

Cys Tyr Tyr Asp Ser Ala Ser Phe Val Lys Glu Gly Leu Gly Lys Leu
        35                  40                  45

Val Ile Asp Glu Leu Glu Pro Ala Leu Gln Phe Cys Asp Tyr Leu Val
    50                  55                  60

Tyr Gly Tyr Ala Gly Ile Glu Arg Asp Ser His Lys Ala Val Ser Leu
65                  70                  75                  80

Asn Gln Gln Leu Asp Leu Asp Leu Gly Lys Gly Leu Tyr Arg Thr Val
                85                  90                  95

Thr Arg Leu Lys Arg Lys Tyr Pro Asn Val Lys Ile Leu Leu Ser Val
            100                 105                 110

Gly Gly Asp Lys Asp Ile Glu Leu Asp Lys Asp Ala Lys Glu Leu Pro
        115                 120                 125

Asn Lys Tyr Leu Glu Leu Leu Glu Ser Pro Thr Gly Arg Thr Arg Phe
    130                 135                 140

Val Asn Thr Val Tyr Ser Leu Val Lys Thr Tyr Gly Phe Asp Gly Leu
145                 150                 155                 160

Asp Val Ala Trp Gln Phe Pro Lys Asn Lys Pro Lys Lys Val His Ser
                165                 170                 175

Gly Ile Gly Asn Leu Trp Lys Gly Phe Lys Lys Val Phe Ser Gly Asp
            180                 185                 190

Ser Ile Val Asp Glu Lys Ser Glu Glu His Lys Glu Gln Phe Thr Ala
        195                 200                 205
```

```
Leu Leu Arg Asp Val Lys Asn Ala Phe Arg Pro Asp Asn Leu Leu Leu
    210                 215                 220

Ser Thr Thr Val Leu Pro Asn Val Asn Ser Ser Leu Phe Tyr Asp Ile
225                 230                 235                 240

Pro Ala Val Val Asn Tyr Leu Asp Phe Val Asn Leu Gly Thr Phe Asp
                245                 250                 255

Phe Phe Thr Pro Gln Arg Asn Pro Glu Ile Ala Asp Tyr Ala Ala Pro
            260                 265                 270

Ile Tyr Glu Leu Ser Glu Arg Asn Pro Glu Phe Asn Val Ala Ala Gln
        275                 280                 285

Val Lys Tyr Trp Leu Arg Asn Asn Cys Pro Ala Ser Lys Ile Asn Val
    290                 295                 300

Gly Val Ala Thr Tyr Gly Arg Pro Trp Lys Leu Thr Asp Asp Ser Gly
305                 310                 315                 320

Asp Thr Gly Val Pro Pro Val Lys Asp Val Lys Asp Glu Ala Pro Val
                325                 330                 335

Gly Gly Asn Thr Gln Val Pro Gly Ile Tyr Ser Trp Pro Glu Val Cys
            340                 345                 350

Ala Leu Leu Pro Asn Gln Asn Asn Ala Tyr Leu Lys Gly Ala Asn Ala
        355                 360                 365

Pro Leu Ile Lys Val Gln Asp Pro Ala Lys Arg Phe Gly Ser Tyr Ala
    370                 375                 380

Tyr Arg Ala Ala Asp Lys Lys Gly Asp Asn Gly Ile Trp Val Ser Phe
385                 390                 395                 400

Glu Asp Pro Asp Thr Ala Ala Asp Lys Ala Gly Tyr Val Arg Thr Glu
                405                 410                 415

Asn Leu Gly Gly Val Ala Leu Phe Asp Leu Ser Tyr Asp Asp Phe Arg
            420                 425                 430

Gly Leu Cys Thr Asn Glu Lys Tyr Pro Ile Leu Arg Ala Ile Lys Tyr
        435                 440                 445

Arg Leu Thr Asn
    450

<210> SEQ ID NO 16
<211> LENGTH: 554
<212> TYPE: PRT
<213> ORGANISM: Manduca sexta

<400> SEQUENCE: 16

Met Arg Ala Thr Leu Ala Thr Leu Ala Val Leu Ala Leu Ala Thr Ala
1               5                   10                  15

Val Gln Ser Asp Ser Arg Ala Arg Ile Val Cys Tyr Phe Ser Asn Trp
                20                  25                  30

Ala Val Tyr Arg Pro Gly Val Gly Arg Tyr Gly Ile Glu Asp Ile Pro
            35                  40                  45

Val Glu Lys Cys Thr His Ile Ile Tyr Ser Phe Ile Gly Val Thr Glu
        50                  55                  60

Gly Asn Ser Glu Val Leu Ile Ile Asp Pro Glu Leu Asp Val Asp Lys
65                  70                  75                  80

Asn Gly Phe Arg Asn Phe Thr Ser Leu Arg Ser Ser His Pro Ser Val
                85                  90                  95

Lys Phe Met Val Ala Val Gly Gly Trp Ala Glu Gly Ser Ser Lys Tyr
            100                 105                 110

Ser His Met Val Ala Gln Lys Ser Thr Arg Met Ser Phe Ile Arg Ser
```

-continued

```
                115                 120                 125
Val Val Ser Phe Leu Lys Lys Tyr Asp Phe Asp Gly Leu Asp Leu Asp
    130                 135                 140

Trp Glu Tyr Pro Gly Ala Ala Asp Arg Gly Gly Ser Phe Ser Asp Lys
145                 150                 155                 160

Asp Lys Phe Leu Tyr Leu Val Gln Glu Leu Arg Arg Ala Phe Ile Arg
                165                 170                 175

Val Gly Lys Gly Trp Glu Leu Thr Ala Ala Val Pro Leu Ala Asn Phe
            180                 185                 190

Arg Leu Met Glu Gly Tyr His Val Pro Glu Leu Cys Gln Glu Leu Asp
        195                 200                 205

Ala Ile His Val Met Ser Tyr Asp Leu Arg Gly Asn Trp Ala Gly Phe
    210                 215                 220

Ala Asp Val His Ser Pro Leu Tyr Lys Arg Pro His Asp Gln Trp Ala
225                 230                 235                 240

Tyr Glu Lys Leu Asn Val Asn Asp Gly Leu His Leu Trp Glu Lys
                245                 250                 255

Gly Cys Pro Ser Asn Lys Leu Val Val Gly Ile Pro Phe Tyr Gly Arg
            260                 265                 270

Ser Phe Thr Leu Ser Ala Gly Asn Asn Asn Tyr Gly Leu Gly Thr Phe
        275                 280                 285

Ile Asn Lys Glu Ala Gly Gly Asp Pro Ala Pro Tyr Thr Asn Ala
    290                 295                 300

Thr Gly Phe Trp Ala Tyr Tyr Glu Ile Cys Thr Glu Val Asp Lys Asp
305                 310                 315                 320

Asp Ser Gly Trp Thr Lys Lys Trp Asp Glu Gln Gly Lys Cys Pro Tyr
                325                 330                 335

Ala Tyr Lys Gly Thr Gln Trp Val Gly Tyr Glu Asp Pro Arg Ser Val
            340                 345                 350

Glu Ile Lys Met Asn Trp Ile Lys Gln Lys Gly Tyr Leu Gly Ala Met
        355                 360                 365

Thr Trp Ala Ile Asp Met Asp Asp Phe Gln Gly Leu Cys Gly Glu Lys
    370                 375                 380

Asn Pro Leu Ile Lys Ile Leu His Lys His Met Ser Ser Tyr Thr Val
385                 390                 395                 400

Pro Pro Pro His Thr Glu Asn Thr Thr Pro Thr Pro Glu Trp Ala Arg
                405                 410                 415

Pro Pro Ser Thr Pro Ser Asp Pro Ser Glu Gly Asp Pro Ile Pro Thr
            420                 425                 430

Thr Thr Thr Ala Lys Pro Ala Ser Thr Thr Lys Thr Thr Val Lys Thr
        435                 440                 445

Thr Thr Thr Thr Thr Ala Lys Pro Pro Gln Ser Val Ile Asp Glu Glu
    450                 455                 460

Asn Asp Ile Asn Val Arg Pro Glu Pro Lys Pro Glu Pro Gln Pro Glu
465                 470                 475                 480

Pro Glu Val Glu Val Pro Pro Thr Glu Asn Glu Val Asp Gly Ser Glu
```

-continued

```
                485                 490                 495
Ile Cys Asn Ser Asp Gln Asp Tyr Ile Pro Asp Lys Lys His Cys Asp
            500                 505                 510

Lys Tyr Trp Arg Cys Val Asn Gly Glu Ala Met Gln Phe Ser Cys Gln
        515                 520                 525

His Gly Thr Val Phe Asn Val Glu Leu Asn Val Cys Asp Trp Pro Ser
    530                 535                 540

Asn Ala Thr Arg Arg Glu Cys Gln Gln Pro
545                 550
```